(12) United States Patent
Rohan

(10) Patent No.: US 11,793,765 B2
(45) Date of Patent: Oct. 24, 2023

(54) VAGINAL FILMS

(71) Applicant: University of Pittsburgh—Of the Commonwealth System of Higher Education, Pittsburgh, PA (US)

(72) Inventor: Lisa Cencia Rohan, Pittsburgh, PA (US)

(73) Assignee: UNIVERSITY OF PITTSBURGH—OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 0 days.

(21) Appl. No.: 16/494,804

(22) PCT Filed: Mar. 27, 2018

(86) PCT No.: PCT/US2018/024505
§ 371 (c)(1),
(2) Date: Sep. 17, 2019

(87) PCT Pub. No.: WO2018/183285
PCT Pub. Date: Oct. 4, 2018

(65) Prior Publication Data
US 2020/0253885 A1 Aug. 13, 2020

Related U.S. Application Data

(60) Provisional application No. 62/573,437, filed on Oct. 17, 2017, provisional application No. 62/477,164, filed on Mar. 27, 2017.

(51) Int. Cl.
| | | |
|---|---|---|
| *A61K 9/70* | (2006.01) | |
| *A61P 31/18* | (2006.01) | |
| *A61K 9/00* | (2006.01) | |
| *A61K 31/505* | (2006.01) | |
| *A61K 31/675* | (2006.01) | |
| *A61K 47/10* | (2017.01) | |
| *A61K 47/38* | (2006.01) | |

(52) U.S. Cl.
CPC .......... *A61K 9/7007* (2013.01); *A61K 9/0031* (2013.01); *A61K 9/0034* (2013.01); *A61K 31/505* (2013.01); *A61K 31/675* (2013.01); *A61K 47/10* (2013.01); *A61K 47/38* (2013.01); *A61P 31/18* (2018.01)

(58) Field of Classification Search
CPC .... A61K 47/38; A61K 31/505; A61K 31/675; A61K 9/7007
See application file for complete search history.

(56) References Cited

U.S. PATENT DOCUMENTS

2011/0112292 A1* 5/2011 Phull .................. C07F 9/65616
544/244
2013/0216590 A1 8/2013 Karim et al.

OTHER PUBLICATIONS

Akil etal (Pharmaceutical Research, 2015, vol. 32, pp. 458-468) (Year: 2015).*
Akil et al (Pharmaceutical Research, Jul. 2014, vol. 32, pp. 458-468) (Year: 2014).*
Agashe et al., "Quick Dissolving Vaginal Film Formulation for Tenofovir", poster presented Apr. 3, 2012.
Akil et al., "Formulation and Characterization of Polymeric Films Containing Combinations of Antiretrovirals (ARVs) for HIV Prevention", Pharm Res, 2014, pp. 458-468, vol. 32.
Baeten et al., "Antiretroviral Prophylaxis for HIV Prevention in Heterosexual Men and Women", The New England Journal of Medicine, 2012, pp. 399-410, vol. 367, No. 5.
Bender Ignacio et al., "Oral and Vaginal Tenofovir for Genital Herpes Simplex Virus Type 2 Shedding in Immunocompetent Women: A Double-Blind, Randomized, Cross-over Trial", Journal of Infectious Diseases, 2015, pp. 1949-1956, vol. 212.
Beringer et al., "Remington: The Science and Practice of Pharmacy, 21st edition", 2005, pp. 871-888, 929-964, 1018-1046, 1626-1684, Lippincott, Williams & Wilkins, Baltimore, MD, Easton, PA.
Bunge et al., "A Phase 1 Trial to Assess the Safety, Acceptability, Pharmacokinetics, and Pharmacodynamics of a Novel Dapivirine Vaginal Film", Journal of Acquired Immune Deficiency Syndromes, 2016, pp. 498-505, vol. 71, No. 5.
Coggins, "Women's preferences regarding the formulation of over-the-counter vaginal spermicides", AIDS, 1998, pp. 1389-1391, vol. 12., No. 11.
Dai et al., "Pharmacological Measures of Treatment Adherence and Risk of HIV Infection in the VOICE Study", The Journal of Infectious Diseases, 2016, pp. 335-342, vol. 213, No. 3.
Dezzutti et al., "HIV-1 Infection of Female Genital Tract Tissue for use in Prevention Studies", Journal of Acquired Immune Deficiency Syndromes, 2013, pp. 548-554, vol. 63, No. 5.
Hendrix et al., "MTN-001: Randomized Pharmacokinetic Cross-Over Study Comparing Tenofovir Vaginal Gel and Oral Tablets in Vaginal Tissue and Other Compartments", PLOS ONE, 2013, Article No. e55013, vol. 8, No. 1.
Hendrix et al., "Dose Frequency Ranging Pharmacokinetic Study of Tenofovir-Emtricitabine After Directly Observed Dosing in Healthy Volunteers to Establish Adherence Benchmarks (HPTN 066)", AIDS Research and Human Retroviruses, 2016, pp. 32-48, vol. 32, No. 1.
Karim et al., "Effectiveness and Safety of Tenofovir Gel, an Antiretroviral Microbicide, for the Prevention of HIV Infection in Women", Science, 2010, pp. 1168-1174, vol. 329, No. 5996.
Kashuba et al., "Genital Tenofovir Concentrations Correlate With Protection Against HIV Infection in the CAPRISA 004 Trial: Importance of Adherence for Microbicide Effectiveness", Journal of Acquired Immune Deficiency Syndromes, 2015, pp. 264-269, vol. 69, No. 3.
Keller et al., "A Randomized Trial to Assess Anti-HIV Activity in Female Genital Tract Secretions and Soluble Mucosal Immunity Following Application of 1% Tenofovir Gel", PLoS One, 2011, Article No. e16475, vol. 6, No. 1.

(Continued)

*Primary Examiner* — Mark V Stevens
(74) *Attorney, Agent, or Firm* — Fish & Richardson P.C.

(57) ABSTRACT

Provided herein are stable, dissolvable films containing active ingredients, such as antimicrobial composition, antiviral compositions, or anti-retroviral compositions for intravaginal or intrarectal placement to provide prophylaxis against viral infections.

11 Claims, 21 Drawing Sheets

(56) References Cited

OTHER PUBLICATIONS

Marrazzo et al., "Tenofovir-Based Preexposure Prophylaxis for HIV Infection among African Women", New England Journal of Medicine, 2015, pp. 509-518, vol. 372, No. 6.

Mngadi et al., "Disclosure of Microbicide Gel use to Sexual Partners: Influence on Adherence in the CAPRISA 004 Trial", AIDS and Behavior, 2014, pp. 849-854, vol. 18, No. 5.

Pirei et al., "Resistance of Herpes Simplex Viruses to Nucleoside Analogues: Mechanisms, Prevalence, and Management", Antimicrobial Agents and Chemotherapy, 2011, pp. 459-472, vol. 55, No. 2.

Raymond et al., "Acceptability of five nonoxynol-9 spermicides", Contraception, 2005, pp. 438-442, vol. 71, No. 6.

Rees et al., "FACTS 001 Phase III Trial of Pericoital Tenofovir 1% Gel for HIV Prevention in Women", Conference on Retroviruses and Opportunistic Infections, 2015, Seattle, WA.

Ross et al., "Use of modern contraception increases when more methods become available: analysis of evidence from 1982-2009", Global Health: Science and Practice, 2013, pp. 203-212, vol. 1, No. 2.

Ross et al., "Access to Contraceptive Methods and Prevalence of Use", Journal of Biosocial Science, 2013, pp. 761-778, vol. 45, No. 6.

Schwartz et al., "Fourteen-day safety and acceptability study of the universal placebo gel", Contraception, 2007, pp. 136-141, vol. 75, No. 2.

Schwartz et al., "A multi-comparlment, single and multiple dose pharmacokinetic study of the vaginal candidate microbicide 1% tenofovir gel", PLoS One, 2011, Article No. e25974, vol. 6, No. 10.

Siemann, "Solvent cast technology—a versatile tool for thin film production", Progress in Colloid Polymer Science, 2005, pp. 1-14, vol. 130.

Succop et al., "Trial participation disclosure and gel use behavior in the CAPRISA 004 tenofovir gel trial", AIDS Care, 2014, pp. 1521-1525, vol. 26, No. 12.

U.S. Department of Health and Human Services, National Institutes of Health, National Institute of Allergy and Infectious Diseases, Division of AIDS. Division of AIDS (DAIDS) Table for Grading the Severity of Adult and Pediatric Adverse Events, Corrected Version 2.1. [Jul. 2017]. Available from: https://rsc.niaid.nih.gov/sites/default/files/daidsgradingcorrectedv21 .pdf.

* cited by examiner

|  | Total (N=78) | Gel Placebo (n=15) | Gel Tenofovir, 40mg (n=16) | Film Placebo (n=16) | Film Tenofovir, 10mg (n=15) | Film Tenofovir, 40 mg (n=16) | P-value* |
|---|---|---|---|---|---|---|---|
| Participants with at least one AE | 70 (89.7%) | 14 (93.3%) | 15 (93.8%) | 14 (87.5%) | 13 (86.7%) | 14 (87.5%) | 0.98 |
| *Gastrointestinal complaint* |  |  |  |  |  |  |  |
| Abdominal discomfort | 9 (11.5%) | 3 (20.0%) | 0 | 1 (6.3%) | 3 (20.0%) | 2 (12.5%) | 0.30 |
| Nausea/Emesis | 3 (3.8%) | 1 (6.7%) | 0 | 0 | 1 (6.7%) | 1 (6.3%) |  |
| Bowel dysfunction | 5 (6.4%) | 1 (6.7%) | 0 | 1 (6.3%) | 1 (6.7%) | 2 (12.5%) |  |
|  | 6 (7.7%) | 1 (6.7%) | 1 (6.3%) | 2 (12.5%) | 1 (6.7%) | 1 (6.3%) |  |
| *Genitourinary complaint* |  |  |  |  |  |  |  |
| Product leakage | 62 (79.5%) | 13 (86.7%) | 15 (93.8%) | 12 (75.0%) | 9 (60.0%) | 13 (81.3%) | 0.21 |
| Pelvic pain | 52 (65.8%) | 13 (86.7%) | 14 (82.4%) | 11 (68.8%) | 6 (40.0%) | 8 (50.0%) | 0.025 |
| Genital itching | 7 (9.0%) | 1 (6.7%) | 1 (6.3%) | 1 (6.3%) | 1 (6.7%) | 3 (18.8%) |  |
| Genital irritation | 6 (7.7%) | 1 (6.7%) | 2 (12.5%) | 0 | 1 (6.7%) | 2 (12.5%) |  |
| Vaginal discharge | 7 (9.0%) | 1 (6.7%) | 2 (12.5%) | 2 (12.5%) | 1 (6.7%) | 1 (6.3%) |  |
| Vaginal odor | 11 (14.1%) | 2 (13.3%) | 1 (6.3%) | 1 (6.3%) | 1 (6.7%) | 6 (37.5%) |  |
| Vaginal infection | 4 (5.1%) | 1 (6.7%) | 0 | 2 (12.5%) | 0 | 1 (6.3%) |  |
| Bleeding abnormality | 4 (5.1%) | 1 (6.7%) | 1 (6.3%) | 0 | 1 (6.7%) | 1 (6.3%) |  |
|  | 8 (10.3%) | 1 (6.7%) | 2 (12.5%) | 1 (6.3%) | 3 (20.0%) | 1 (6.3%) |  |
| AE Severity (any body system) |  |  |  |  |  |  |  |
| Any Grade 1 | 70 (89.7%) | 14 (93.3%) | 15 (93.8%) | 14 (87.5%) | 13 (86.7%) | 14 (87.5%) | 0.98 |
| Any Grade 2 | 11 (14.1%) | 1 (6.7%) | 2 (12.5%) | 1 (6.3%) | 3 (20.0%) | 4 (25.0%) | 0.54 |
| Any Grade 3 | 1 (1.3%) | 0 | 0 | 0 | 0 | 1 (6.3%) | -- |
| AE Relatedness to Study Product (any body system) |  |  |  |  |  |  |  |
| Any Related | 58 (74.4%) | 13 (86.7%) | 15 (93.8%) | 11 (68.8%) | 8 (53.3%) | 11 (68.8%) | 0.07 |
| Any Not Related | 40 (51.3%) | 7 (46.7%) | 8 (50.0%) | 8 (50.0%) | 9 (60.0%) | 8 (50.0%) | 0.96 |

FIG. 7

| Product Name/ Description: Tenofovir Vaginal Film 40mg Dose | | Batch No: 11496 | Item No: 01-263-0008 | Storage Conditions: 25°C/60%RH | Stability Protocol PDP-2013-0047 | | | | | Study Initiation 11/20/2013 | |
|---|---|---|---|---|---|---|---|---|---|---|---|
| | | | CoA | | Time Point (Months)/Pull Date | | | | | | |
| Test | Method | Specification | Initial | 3 | 6 | 9 | 12 | 18 | 24 | | |
| Appearance | Visual | ** | Conforms | Conforms | Conforms | Conforms | Conforms | Conforms | Conforms | | |
| Strip Weight | Calibrated Balance | Target = 382.1mg (343.9-420.3mg) | 391.2mg | 384.8mg | 387.0mg | 386.8mg | 392.0mg | 385.1mg | 385.2mg | | |
| Strip Thickness | Calibrated Micrometer | Report Results | 111 μm | 105 μm | 115 μm | NTD | 126 μm | 120 μm | 110 μm | | |
| Elongation Break | Current Innoteq Method 11-78 | Report Results | 22% | 34% | 31% | NTD | 31% | 37% | 28% | | |
| Loss on Drying | Current USP<731> | Report Results | 10.7% | 9.3% | 10.2% | NTD | 10.1% | 9.0% | 9.0% | | |
| Assay | Current Innoteq Method 11-72 | 90-110% of label claim | 102% | 100% | 100% | 100% | 101% | 104% | 98% | | |
| Impurities | Current Innoteq Method 11-72 | Total: Report Results | None Detected | 0.03% | 0.04% | None Detected | None Detected | None Detected | None Detected | | |
| | | Individual: Report Results by RRT | None Detected | RRT: 0.75 0.03% | RRT: 0.72 0.04% | None Detected | None Detected | None Detected | None Detected | | |
| Drug Release | Current Innoteq Method 11-77 | Report Results | 30 min Mean: 99% | 30 min Mean: 96% | 30 min Mean: 100% | NTD | 30 min Mean: 101% | 30 min Mean: 101% | 30 min Mean: 99% | | |
| Total Aerobic Microbial Count | Current USP <61> | NMT 100 CFU/g | <10 CFU/g | NTR | NTR | NTR | <10 CFU/g | NTR | <10 CFU/g | | |

FIG. 11A

| Test | Method | Specification | Time Point (Months) | | | | | | | |
|---|---|---|---|---|---|---|---|---|---|---|
| | | | CoA | | | | | | | |
| | | | 0 | 3 | 6 | 9 | 12 | 18 | 24 | |
| Total Combined Yeasts and Mold Counts | Current USP <61> | NMT 10 CFU/g | <10 CFU/g | NTR | NTR | NTR | <10 CFU/g | NTR | <10 CFU/g | |
| Salmonella | Current USP <62> | Absent | Absent | NTR | NTR | NTR | Absent | NTR | Absent | |
| Escherichia Coli | Current USP <62> | Absent | Absent | NTR | NTR | NTR | Absent | NTR | Absent | |
| Staphylococcus aureus | Current USP <62> | Absent | Absent | NTR | NTR | NTR | Absent | NTR | Absent | |
| Pseudomonas aeruginosa | Current USP <62> | Absent | Absent | NTR | NTR | NTR | Absent | NTR | Absent | |
| Candida albicans | Current USP <62> | Absent | Absent | NTR | NTR | NTR | Absent | NTR | Absent | |

NTR = No testing required as per protocol. ND = None Detected. NTD = Not tested as explained per deviation DR15-087.
* Clear to Translucent, Colorless to Off-white Square Flexible Films

FIG. 11B

| Product Name/ Description: Tenofovir Vaginal Film 10mg Dose | | Batch No: 11495 | Item No: 01-263-0007 | Storage Conditions: 25°C/60%RH | | Stability Protocol PDP-2013-0047 | | | Study Initiation 11/20/2013 | |
|---|---|---|---|---|---|---|---|---|---|---|
| | | | | | | Time Point (Months)/Pull Date | | | | |
| | | | CoA | | | | | | | |
| Test | Method | Specification ** | 0 | 3 | 6 | 9 | 12 | 18 | 24 |
| Appearance | Visual | ** | Conforms | Conforms | Conforms | Conforms | Conforms | Conforms | Conforms |
| Strip Weight | Calibrated Balance | Target = 346.3mg (311.7-380.9mg) | 364.5mg | 356.7mg | 357.4mg | 386.8mg | 392.0mg | 350.6mg | 346.9mg |
| Strip Thickness | Calibrated Micrometer | Report Results | 105 μm | 105 μm | 113 μm | NTD | 158 μm | 103 μm | 90 μm |
| Elongation Break | Current Innoteq Method 11-78 | Report Results | 37% | 27% | 33% | NTD | 20% | 30% | 15% |
| Loss on Drying | Current USP<731> | Report Results | 13% | 12.2% | 13.4% | NTD | 14.1% | 10.1% | 12.1% |
| Assay | Current Innoteq Method 11-72 | 90-110% of label claim | 103% | 101% | 98% | 102% | 98% | 100% | 97% |
| Impurities | Current Innoteq Method 11-72 | Total: Report Results | 0.10% | 0.03% | 0.08% | None Detected | None Detected | None Detected | None Detected |
| | | Individual: Report Results by RRT | RRT: 1.75 0.10% | RRT: 0.75 0.03% | RRT: 0.69 0.04% RRT: 0.72 0.04% | None Detected | None Detected | None Detected | None Detected |
| Drug Release | Current Innoteq Method 11-77 | Report Results | 30 min Mean: 105% | 30 min Mean: 98% | 30 min Mean: 98% | 30 min Mean: 103% | 30 min Mean: 103% | 30 min Mean:98% | 30 min Mean: 98% |
| Total Aerobic Microbial Count | Current USP <61> | NMT 100 CFU/g | <10 CFU/g | NTR | NTR | NTR | <10 CFU/g | NTR | <10 CFU/g |

** Clear to Translucent, Colorless to Off-white Square Flexible Film

FIG. 11C

| Test | Method | Pull Date | | Time Point (Months) | | | | | | |
|---|---|---|---|---|---|---|---|---|---|---|
| | | Specification | CoA | | | | | | | |
| | | | 0 | 3 | 6 | 9 | 12 | 18 | 24 | |
| Total Combined Yeasts and Mold Counts | Current USP <61> | NMT 10 CFU/g | <10 CFU/g | NTR | NTR | NTR | <10 CFU/g | NTR | <10 CFU/g | |
| Salmonella | Current USP <62> | Absent | Absent | NTR | NTR | NTR | Absent | NTR | Absent | |
| Escherichia Coli | Current USP <62> | Absent | Absent | NTR | NTR | NTR | Absent | NTR | Absent | |
| Staphylococcus aureus | Current USP <62> | Absent | Absent | NTR | NTR | NTR | Absent | NTR | Absent | |
| Pseudomonas aeruginosa | Current USP <62> | Absent | Absent | NTR | NTR | NTR | Absent | NTR | Absent | |
| Candida albicans | Current USP <62> | Absent | Absent | NTR | NTR | NTR | Absent | NTR | Absent | |

NTR = No testing required as per protocol. ND = None Detected. NTD = Not tested as explained per deviation DR15-087.
* Clear to Translucent, Colorless to Off-white Square Flexible Films

FIG. 11D

| Product Name/ Description: Tenofovir Vaginal Film 40mg Dose | | Batch No: 11496 | Item No: 01-263-0008 | Storage Conditions: 40°C/75%RH | | Stability Protocol PDP-2013-0047 | | Study Initiation 11/20/2013 |
|---|---|---|---|---|---|---|---|---|
| | | | | Time Point (Months)/Pull Date | | | | |
| | | | CoA | | | | | |
| Test | Method | Specification | 0 | 1 | 2 | 3 | | 6 |
| Appearance | Visual | ** | Conforms | Conforms | Conforms | Conforms | | Conforms |
| Strip Weight | Calibrated Balance | Target = 382.1mg (343.9-420.3mg) | 391.2mg | 390.0mg | 388.2mg | 388.6mg | | 389.6mg |
| Strip Thickness | Calibrated Micrometer | Report Results | 111 μm | 103 μm | 116 μm | 104 μm | | 109 μm |
| Elongation Break | Current Innoteq Method 11-78 | Report Results | 22% | 34% | 31% | 31% | | 32% |
| Loss on Drying | Current USP<731> | Report Results | 10.7% | 11.0% | 6.3% | 9.9% | | 9.8% |
| Assay | Current Innoteq Method 11-72 | 90-110% of label claim | 102% | 101% | 92% | 100% | | 100% |
| Impurities | Current Innoteq Method 11-72 | Total: Report Results | None Detected | 0.07% | None Detected | 0.09% | | 0.07% |
| | | Individual: Report Results by RRT | None Detected | RRT: 1.76 0.07% | None Detected | RRT: 0.75 0.09% | | RRT: 0.69 0.03% RRT: 0.72 0.14% |
| Drug Release | Current Innoteq Method 11-77 | Report Results | 30 min Mean: 99% | 30 min Mean: 99% | 30 min Mean: 95% | 30 min Mean: 94% | | 30 min Mean: 91% |

** Clear to Translucent, Colorless to Off-white Square Flexible Film

FIG. 12A

| Product Name/Description:<br>Tenofovir Vaginal Film 10mg Dose | | Batch No:<br>11495 | Item No:<br>01-263-0007 | Storage Conditions:<br>40°C/75%RH | Stability Protocol<br>PDP-2013-0047 | | Study Initiation<br>11/20/2013 |
|---|---|---|---|---|---|---|---|
| | | Pull Date | CoA | Time Point (Months)/Pull Date | | | |
| Test | Method | Specification | 0 | 1 | 2 | 3 | 6 |
| Appearance | Visual | * | Conforms | Conforms | Conforms | Conforms | Conforms |
| Strip Weight | Calibrated Balance | Target =346.3mg (311.7-380.9mg) | 364.5mg | 349.4mg | 347.1mg | 351.7mg | 362.1mg |
| Strip Thickness | Calibrated Micrometer | Report Results | 105 μm | 103 μm | 116 μm | 106 μm | 109 μm |
| Elongation Break | Current Innoteq Method 11-78 | Report Results | 37% | 27% | 26% | 28% | 25% |
| Loss on Drying | Current USP<731> | Report Results | 13.0% | 14.4% | 10.3% | 12.6% | 12.5% |
| Assay | Current Innoteq Method 11-72 | 90-110% of label claim | 103% | 98% | 91% | 100% | 102% |
| Impurities | Current Innoteq Method 11-72 | Total: Report Results | 0.10% | 0.13% | None Detected | 0.04% | 0.07% |
| | | Individual: Report Results by RRT | RRT: 1.75 0.10% | RRT: 1.76 0.13% | None Detected | RRT: 0.75 0.04% | RRT: 0.72 0.07% |
| Drug Release | Current Innoteq Method 11-77 | Report Results | 30 min Mean: 105% | 30 min Mean: 96% | 30 min Mean: 93% | 30 min Mean: 94% | 30 min Mean: 98% |

* Clear to Translucent, Colorless to Off-white Square Flexible Film

FIG. 12B

| DV10 | Animal # | | Monday D1 pre-Film | Monday D1 post-Film | Tuesday Day 2 | Wednesday Day 3 | Thursday Day 4 | Friday Day 5 | Monday Day 8 |
|---|---|---|---|---|---|---|---|---|---|
| Dosing Blue dye | Macaque 1 | | | | | | | | |
| Standard Thick Film | | Blue dye | absent | present | present | absent | | | |
| | | TFV ng/swab | BLQ | na | 66375.00 | 7625.00 | na | 240.00 | 7.70 |
| | Macaque 2 | | | | | | | | |
| | | Blue dye | absent | present | present | absent | | | |
| | | TFV ng/swab | BLQ | na | 88500.00 | 14875.00 | 3725.00 | 422.50 | 17.45 |
| | Macaque 3 | | | | | | | | |
| | | Blue dye | absent | present | absent | | | | |
| | | TFV ng/swab | BLQ | na | 47.75 | 24.58 | 17.43 | 27.75 | 5.85 |
| | Macaque 4 | | | | | | | | |
| | | Blue dye | absent | present | present | absent | | | |
| | | TFV ng/swab | BLQ | na | 32500.00 | 4862.50 | 1166.25 | 635.00 | 2.70 |

FIG. 16

| PV10 | Animal ID | Monday D1 pre-film | Monday post-film | Tuesday Day 2 | Wednesday Day 3 | Thursday Day 4 | Friday Day 5 | Monday Day 8 |
|---|---|---|---|---|---|---|---|---|
| Dosing Blue dye | | | | | | | | |
| 5X Thick Film | Macaque 1 Blue dye | absent | present | absent | na | na | na | na |
| | Macaque 1 TFV ng/swab | BLQ | 627.50 | 39.25 | 51.75 | 15.45 | 3.20 | |
| | Macaque 2 Blue dye | absent | present | present | present | present | absent | na |
| | Macaque 2 TFV ng/swab | BLQ | 55250.00 | 14125.00 | 2400.00 | 37.25 | 6.73 | |
| | Macaque 3 Blue dye | absent | present | present | present | absent | na | na |
| | Macaque 3 TFV ng/swab | BLQ | 132500.00 | 20500.00 | 7662.50 | 1312.50 | 9.15 | |
| | Macaque 4 Blue dye | absent | present | present | absent | na | na | na |
| | Macaque 4 TFV ng/swab | 0.76 | BLQ | BLQ | BLQ | BLQ | BLQ | |

FIG. 17

VAGINAL FILMS

CROSS-REFERENCE TO RELATED APPLICATIONS

This application is the United States national phase of International Application No. PCT/US2018/024505 filed Mar. 29, 2019, and claims priority to United States Provisional Patent Application Nos. 62/477,164 and 62/573,437, filed Mar. 27, 2017 and Oct. 17, 2017, respectively, each of which is hereby incorporated by reference in its entirety.

STATEMENT REGARDING FEDERALLY SPONSORED RESEARCH

This invention was made with government support under Grant No. AI082639 awarded by the National Institutes of Health. The government has certain rights in the invention.

BACKGROUND OF THE INVENTION

Field of the Invention

The present invention relates to pharmaceutical vehicles for use in delivering therapeutic compositions to patients. More particularly, the present invention relates to films for the delivery of antiviral compositions to patients.

Description of Related Art

Microbicides may be candidates applied vaginally or rectally for protection from sexually transmitted infections, including human immunodeficiency virus (HIV) infection. Preexposure prophylaxis (PrEP) with oral Truvada® (emtricitabine 200 mg/tenofovir disoproxil fumarate 300 mg)/emtricitabine reduces HIV acquisition in women who demonstrate high adherence to the daily medication. Likewise, when used consistently, vaginal tenofovir (TFV) gel can confer protection. One clinical trial of vaginal TFV gel demonstrated efficacy across the entire study population of sexually active women. In that randomized placebo controlled trial, women were instructed on peri-coital use of the vaginal gel: the first dose within 12 hours of sexual activity and then a second dose as soon as possible after intercourse, but within 12 hours. HIV incidence in the group using TFV gel was lower than when a placebo gel was used. In women with high adherence (greater than 80% of sex acts covered by study product), HIV incidence was significantly lower. Subsequent analyses demonstrated that women with high TFV concentrations in the cervico-vaginal fluid experienced better protection.

Even in trials of vaginal TFV gel which did not show a protective effect, sub-analyses suggest that for higher adherers, some protection was afforded. Understanding that adherence is central to PrEP effectiveness, developing a product that is easy to use and supports high adherence is an important objective. Significant efforts have been directed towards developing sustained delivery products such as injectables and vaginal rings which may improve adherence by reducing user error. However, not all women who would potentially use an HIV prevention product would necessarily choose a long-acting product. Some women may have infrequent sexual exposures and may desire HIV protection only during times of sexual activity; therefore, there is still a recognized need for on-demand microbicide products.

Vaginal tenofovir (TFV) gel also can confer prophylactic protection against herpes simplex virus (HSV) types 1 and 2 (HSV-1 and HSV-2, respectively) infections (See, e.g., Bender-Ignacia, RA, Oral and Vaginal Tenofovir for Genital Herpes Simplex Virus Type 2 Shedding in Immunocompetent Women: A Double-Blind, Randomized, Cross-over Trial. (2015) J. Infect. Dis. 212(12):1949-56). A vaginal drug delivery platform that permits on-demand microbicide drug delivery, as well as on-demand delivery of active agents in general, is desirable to certain women.

SUMMARY OF THE INVENTION

In view of the shortcomings in the field, dissolvable vaginal film formulations of topical microbicides may provide an attractive alternative by delivering equivalent drug to the vagina while being more acceptable to women because of less leakage. Accordingly, provided herein is a dissolvable film for intravaginal delivery of an active agent, for example an antiretroviral composition, e.g. for treatment or prophylaxis of HIV or an antiviral composition, e.g., for treatment of a herpesvirus, such as a HSV, e.g. HSV-1 and/or HSV-2.

BRIEF DESCRIPTION OF THE DRAWINGS

FIG. 7. Incidence of adverse events (AEs) by study arm.

FIG. 11A-11D. Stability of (A-B) 40 mg TFV film and (C-D) 10 mg TFV film at 25 degrees Celsius and 60% relative humidity.

FIG. 12A-12B. Stability of (A) 40 mg TFV film and (B) 10 mg TFV film at 40 degrees Celsius and 75% relative humidity.

FIG. 16 shows visualization of films and concentrations of TFV in vaginal fluid over time for films according to aspects of the film described herein.

FIG. 17 shows visualization of films and concentrations of TFV in vaginal fluid over time for films according to aspects of the film described herein.

DESCRIPTION OF THE INVENTION

Figure 1:
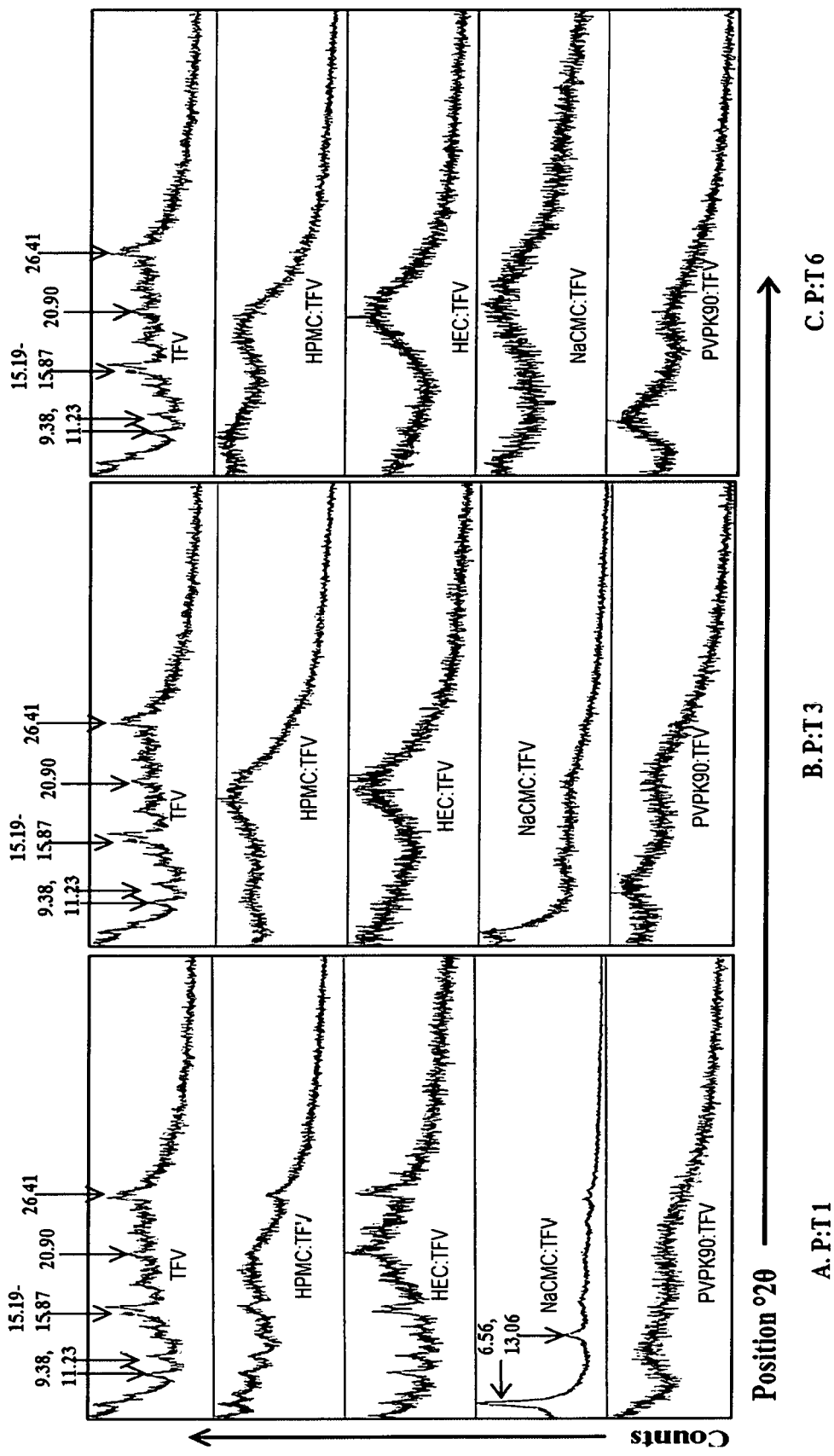
FIG. 1. X-ray diffraction (XRD) pattern of polymer:TFV (P:T) lyophilized mass at different ratio. Columns A, B, and C represent P:T ratio 1, 2 and 3, respectively. The top row represents the XRD pattern for lyophilized TFV. In the rows below, the change in the XRD patterns of TFV in presence of various polymers are shown.

The following description is merely exemplary in nature and is in no way intended to limit the invention, its application, or uses. While the description is designed to permit one of ordinary skill in the art to make and use the invention, and specific examples are provided to that end, they should in no way be considered limiting. It will be apparent to one of ordinary skill in the art that various modifications to the following will fall within the scope of the appended claims. The present invention should not be considered limited to the presently disclosed aspects, whether provided in the examples or elsewhere herein.

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of ranges is intended as a continuous range including every value between the minimum and maximum values. As used herein "a" and "an" refer to one or more.

As used herein, the term "patient" or "subject" refers to members of the animal kingdom including but not limited to human beings and "mammal" refers to all mammals, including, but not limited to human beings.

As used herein, the "treatment" or "treating" of a wound or defect means administration to a patient by any suitable dosage regimen, procedure and/or administration route an amount of a composition, device or structure effective to, and with the object of achieving a desirable clinical/medical end-point, including attracting progenitor cells, healing a wound, correcting a defect, etc.

As used herein, the terms "comprising," "comprise" or "comprised," and variations thereof, are open ended and do not exclude the presence of other elements not identified. In contrast, the term "consisting of" and variations thereof is intended to be closed, and excludes additional elements in anything but trace amounts.

As used herein, a "polymer" is a compound formed by the covalent joining of smaller molecules, which are referred to herein as monomers before incorporation into the polymer and residues, or polymer subunits, after incorporated into a polymer. A "copolymer" is a polymer comprising two or more different residues. A polymer "comprises" or is "derived from" a stated monomer if that monomer is incorporated into the polymer. Thus, the incorporated monomer that the polymer comprises is not the same as the monomer prior to incorporation into a polymer, in that at the very least, certain terminal groups or atoms are incorporated into the polymer backbone or are excised. A polymer is said to comprise a specific type of linkage, such as an ester, or urethane linkage, if that linkage is present in the polymer.

Provided herein are stable pharmaceutical compositions (e.g. drug products) in the form of thin-film dosage forms of various therapeutic compositions that are advantageously delivered through mucosal tissue, for example vaginal or rectal mucosal tissue. The thin-films disclosed herein can be formulated to be rapidly dissolving or to dissolve in a controlled fashion over time by altering the geometry of the film (e.g., changing thickness).

Therapeutic compositions/active ingredients useful in the thin films described herein can include, but are not limited to, antiretroviral compositions (e.g., nucleoside reverse transcriptase inhibitors, nonnucleoside reverse transcriptase inhibitors, protease inhibitors, fusion inhibitors, entry inhibitors, and integrase strand transfer inhibitors, such as, for example and without limitation, efavirenz, emtricitabine, rilpivirine, atazanavir sulfate, darunavir ethanolate, elvitegravir, lamivudine, zidovudine, abacavir, zalcitabine, dideoxycytidine, azidothymidine, didanosine, dideoxyinosine, stavudine, rilpivirine, etravirine, delvaridine, nevirapine, amprenavir, tipranavir, inidinavir, saquinavir, lopinavir, ritonavir, fosamprenavir, ritonavir, darunavir, atazanavir, nelfinavir, enfuvirtide, raltegravir, dolutegravir, elvitegravir, maraviroc, DS003, tenofovir (TFV), TFV alefanamide, TFV disoproxil fumarate, and dapivirine), antiviral compositions (e.g., 4'-Ethynyl-2-fluoro-2'-deoxyadenosine (EFdA), nucleoside analogs, such as: acyclovir (2-amino-9-(2-hydroxyethoxymethyl)-3H-purin-6-one), penciclovir (2-amino-9-[4-hydroxy-3-(hydroxymethyl)butyl]-3H-purin-6-one), foscarnet (phosphonoformic acid), cidofovir ([(2S)-1-(4-amino-2-oxopyrimidin-1-yl)-3-hydroxypropan-2-yl] oxymethylphosphonic acid), adefovir (2-(6-aminopurin-9-yl)ethoxymethylphosphonic acid), and pharmaceutically-acceptable ester prodrugs thereof, such as valaciclovir (valine aciclovir ester, 2-[(2-amino-6-oxo-3H-purin-9-yl) methoxy]ethyl (2S)-2-amino-3-methylbutanoate) or famciclovir ([2-(acetyloxymethyl)-4-(2-aminopurin-9-yl)butyl] acetate)), antibiotic/antiprotozoal compositions (e.g., GRFT, CSIC, metronidazole), antifungal compositions (e.g., clotrimazole), hormones or hormonal compositions (e.g., levonorgestrel, etonogrestrel, desogrestrel, dienogest), and hormonal receptor modulators (e.g., ulipristal acetate). In addition, other compounds such as RANTES derivatives and retrocyclin (e.g., RC-101) can be included. Compositions that affect metabolism of another composition, such as antiretroviral compositions, such as cobicistat (sold under the trade name Tyboost®) can also be included. For example, a composition in a film as described herein can include atazanavir and cobicistat (sold under the trade name Evotaz®).

Those of skill in the art will appreciate that the aforementioned examples are non-limiting, and that any therapeutic composition, including antiviral, antiretroviral, antibacterial, antiprotozoal, antifungal, or hormone-based therapeutics, can advantageously be included in films as described herein.

In a non-limiting aspect, the film is a stable pharmaceutical composition in the form of a film for the delivery of TFV (including TFV pharmaceutical salt forms), optionally in combination with another pharmaceutically active agent, for example, dapivirine. TFV can be provided as 9-[9(R)-2-(phosphonomethoxy)propyl]adenine (PMPA), tenofovir disoproxil, or the prodrug tenofovir alafenamide. The salt forms, for example fumarate salt forms, of either composition can be included in films as described herein. For ease of reference, references herein will be made to "tenofovir" or TFV, with the understanding that the term can refer to PMPA, tenofovir disoproxil or tenofovir alafenamide, as well as salts thereof. In non-limiting aspects, a film as described herein includes one or both of TFV and dapivirine. A film as described herein is particularly suitable for vaginal or rectal placement, and for preexposure prophylaxis (PrEP) to reduce HIV or HSV acquisition. While vaginal placement is exemplified in the following disclosure, the film is equally suitable for rectal placement for PrEP. In one aspect, the film is thin, facilitating rapid and complete delivery of the active agent (e.g., TFV) within minutes to hours, or thicker, resulting in release over a day or more.

The dissolvable film disclosed herein includes one or more polymers that allow for a mechanically robust, stable, yet easily-dissolvable matrix for the therapeutic composition. In one aspect, the film is formed from one or more cellulosic polymers, which are desirable for their biocompatible nature, including the lack of negative effect they, and their metabolites, have on innate lactobacilli flora and epithelium in the vagina. Any cellulosic, e.g. cellulose-based, polymer may be useful in preparing films as described herein. In aspects, the useful cellulosic polymers include carboxymethylcellulose, hydroxypropyl methylcellulose, hydroxy propyl cellulose, and hydroxyethyl cellulose. In certain aspects the film further includes a non-cellulose polymer. In some aspects, the non-cellulose polymer is polyvinyl pyrrolidone (PVP) or polyvinyl alcohol (PVA), polysaccharide polymers such as pullulan, polyacrylic acid polymers such as carbopol, and polymers including polyethylene glycol. In a non-limiting aspect, the film includes carboxymethylcellulose (CMC or NaCMC), hydroxypropyl methylcellulose (HMC or HPMC), hydroxyethyl cellulose (HEC), and polyvinyl pyrrolidone.

To achieve a stable and easily-dissolvable film, the various polymer components can be combined in a specific ratio or range for each component. In aspects the film includes HEC:HMC:CMC in a weight ratio such as (0.75-1.25):(0.75-1.25):(0.25-0.5). In some aspects, the film includes HEC:HMC:CMC in a weight ratio of, for example and without limitation, 1:1:0.33. In aspects, the polymers comprise between 12-18% by wt. of a pre-film solution (polymers and solvent), all subranges therebetween inclusive. In a non-limiting aspect, the film includes 6% wt. HEC, 6% wt. HPMC, and 2% wt. NaCMC.

In addition to the polymer base of the film matrix, a film as described herein can include one or more additional components, for example, and without limitation, a plasticizer, a dispersant, a humectant, and/or a disintegrant. Suitable plasticizers for use in a film as described herein include glycerin, polyethylene glycol, polyethylene glycol monomethyl ether, propylene glycol, sorbitol sorbitan solution, diacetylated monoglycerides, castor oil, phthalates (such as bis(2-ethylhexyl) phthalate or diethyl phthalate), triethyl citrate, tributyl citrate, trihexyl citrate, trioctyl citrate, diesters of dicarboxylic acids (such as sebacic acid or azelaic acid), and esters of glycerol (such as triacetin such as tributyrin). Suitable disintegrants include polyethylene glycol (PEG), such as PEG 400, PEG 6000, and PEG 8000. In aspects in which a plasticizer, dispersant, humectant, and/or disintegrant is included, the formulation can include 1.5-4.4% wt. of such additive(s). In aspects the film can include cellulose polymers and plasticizer in a ratio of (0.75-1.25):(0.75-1.25):(0.25-0.5):(0.25-0.5), in some aspects in a ratio of 1:1:0.33:0.33 (HEC:HMC:CMC:plasticizer). In a non-limiting aspect, the pre-film solution includes 6% wt. HEC, 6% wt. HPMC, 2% wt. NaCMC, and 2% wt. glycerin.

In use, the polymers, active ingredient(s), and (if utilized) plasticizers, dispersants, humectants, and/or disintegrants may be admixed with any pharmaceutically acceptable carrier(s) or excipient(s) customarily used for administration of drugs to the patient in question (see, generally, Troy, D B, Editor, Remington: The Science and Practice of Pharmacy, 21st Ed., Lippincott Williams & Wilkins (2005), pp. 871-888, 929-964, and 1018-1046, and 1626-1684 for non-limiting examples of various dosage forms, manufacturing methods, useful therapeutics, and useful analyses for designing a film for administration as described herein.

A film according to the present invention is utilized to deliver an amount effective of a therapeutic composition. An "amount effective" for treatment of a condition is an amount of an active agent or dosage form, effective to achieve a determinable end-point. The "amount effective" is preferably safe—at least to the extent the benefits of treatment outweighs the detriments and/or the detriments are acceptable to one of ordinary skill and/or to an appropriate regulatory agency, such as the U.S. Food and Drug Administration. Using the teachings of the present disclosure, a person of ordinary skill in the arts can prepare the film described herein, and titrate the effect on any objectively-determinable end-point, for instance first in an animal model and later in humans. As shown in the Examples below, an example of an "amount effective" is indicated. In aspects, an "amount effective" is greater than or equal to 1 ng, 10 mg, 100 ng, 500 ng, 1 mg, 2 mg, 3 mg, 4 mg, 5 mg, 10 mg, 20 mg, 30 mg, or 40 mg, all doses and ranges therebetween inclusive, such as ranging from 1 ng to 100 mg, from 100 ng to 50 mg, or from 1 mg to 40 mg.

Those of skill in the art will appreciate that depending on the amount of therapeutic (e.g., antiviral) composition to be delivered, the concentration in the film itself, and the dimensions of the film, will necessarily be adjusted accordingly; however, the selection of polymer will also affect the ultimate amount of active ingredient that can be used. In development of one aspect of a film described herein, polymer:antiretroviral (P:T ratio) ratios of 0.5-6 were investigated. It was shown that ratios that provided suitable solubility of an antiretroviral composition had suitable P:T ratios that varied based on the polymers used. For example a ratio of 6:1 is suitable for HPMC, HEC, and PVP, while for methylcellulose and PVA a ratio of 4:1 was identified as suitable. In aspects, the pre-film solution includes 6% wt. HEC, 6% wt. HPMC, 2% wt. NaCMC, 2% wt. glycerin, and 0.5% wt. of an antiretroviral composition. In a non-limiting aspect, the pre-film solution includes 6% wt. HEC, 6% wt. HPMC, 2% wt. NaCMC, 2% wt. glycerin, and 2% wt. of an antiretroviral composition (i.e. a P:T ratio of 3:1). FIG. 1 shows XRD patterns for films of various P:T ratios. A useful ratio for forming a useful film as described herein is drug to polymer ratio. While any ratio of drug to CMC can be usable, in aspects in which HEC and HPMC are used, a useful ratio is in the range of 1:2 to 1:6, all subranges therebetween inclusive.

Also disclosed herein are methods of manufacturing a dissolvable film for intravaginal delivery of an antiviral composition. Useful methods for producing a film as described herein include solvent casting. Solvent-casting techniques are known to those of skill in the art (see, e.g., Siemann, Solvent cast technology—a versatile tool for thin film production. *Progr Colloid Polymer Sci* 2005; 130: 1-4). In that method, all ingredients are mixed in a solvent, for example purified water, in a specific addition order. The homogenous blend is then poured (cast) onto a heated surface and dried at a specific thickness to obtain thin polymeric film. The TFV film composition comprising a combination of TFV with a desirable ratio of selected polymers provides thin strips with clear to off-white color, softness, and the TFV is present in the solubilized state in the film and uniformly distributed throughout the film. The films are stable and maintain a desirable shelf life without TFV crystallization and discoloration.

As noted above, the ratio of components included in the film imparts to the drug product mechanical robustness, stability, and dissolvability. Viscosity of the pre-film solution influences the formation of the film, thus, in aspects, the polymer components are within a tight ratio window. In addition, the solvent casting process, including order of addition, is relevant. Without regard for these parameters, TFV can be destabilized through crystallization, rendering the product unsuitable for any substantial shelf-life.

A non-limiting protocol for forming a film as described herein includes dissolving all the components in an appropriate solvent. Suitable solvents may be aqueous or organic in nature including, for example and without limitation, water, acetone, or ethanol. The order of component addition depends on the physical and chemical properties of the component, as well as the selected solvent. The active ingredient (e.g. antiretroviral) can be added to the polymer solution at various times dependent on the requirements of the composition. In many cases it is dissolved or suspended into the polymer-plasticizer. During mixing, entrapment of air in the solution can occur, and this can be eliminated using centrifugation or sonication for small batches or vacuumed for large scale production. Once the film solution is homogenous, it is then cast onto a substrate and the film solution is dried. The drying process can occur at ambient temperature or at accelerated temperature by direct heat or using a vacuum oven. The drying process is defined for each specific formulation during film formulation development. Once the film sheets are prepared, they can be cut into individual unit doses using a die press. The dimensions and shape of the film can be determined as needed, depending on the pharmacological application. Films can also be generated by directly applying the film solution into individual film molds.

Figure 2:
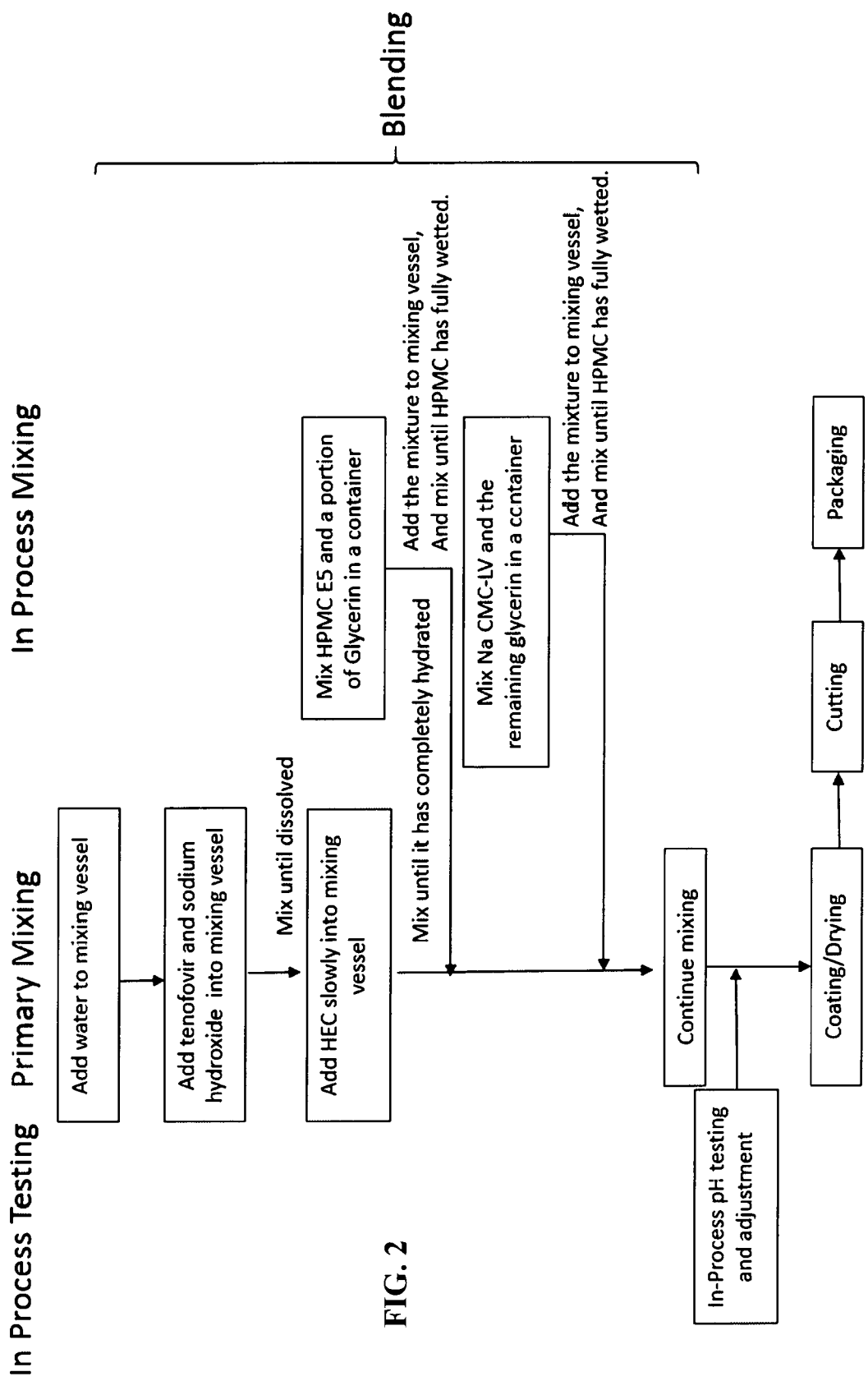
FIG. 2. A flowchart providing one aspect of a method as described herein.

A non-limiting protocol for producing a film as described herein is represented in FIG. 2. The protocol includes, under constant mixing, adding accurately quantified amounts of a solubilizing, or alkalinizing, agent known to those of skill in the art, such as sodium hydroxide, and the active agent (e.g., antiretroviral), in a solvent, such as water, until dissolution. The solubilizing/alkalinizing agent aids in solubilization of the antiretroviral agent. Next, accurately quantified amounts of the polymers are added to the solution. For example, HEC is added until it is completely hydrated, followed by addition of a pre-mix of HPMC and a plasticizer, such as glycerin, to the solution until the HPMC is fully wetted. Afterwards, a premix of CMC and the remaining amount of plasticizer is added to the solution until the CMC is fully wetted. After further mixing the pH is tested and, if necessary, adjusted to provide a final pH of 5-8, in some aspects 6-8, and, in some aspects 6-6.5, all ranges there between inclusive, using, e.g., sodium hydroxide. Films prepared from a solution having a pH below 5, for example 4.8, showed unacceptable crystallization of the antiretroviral. While triethanolamine (TEA) can be used to adjust pH, film discoloration can result and therefore, in some aspects, the protocol excludes TEA.

Figure 3:
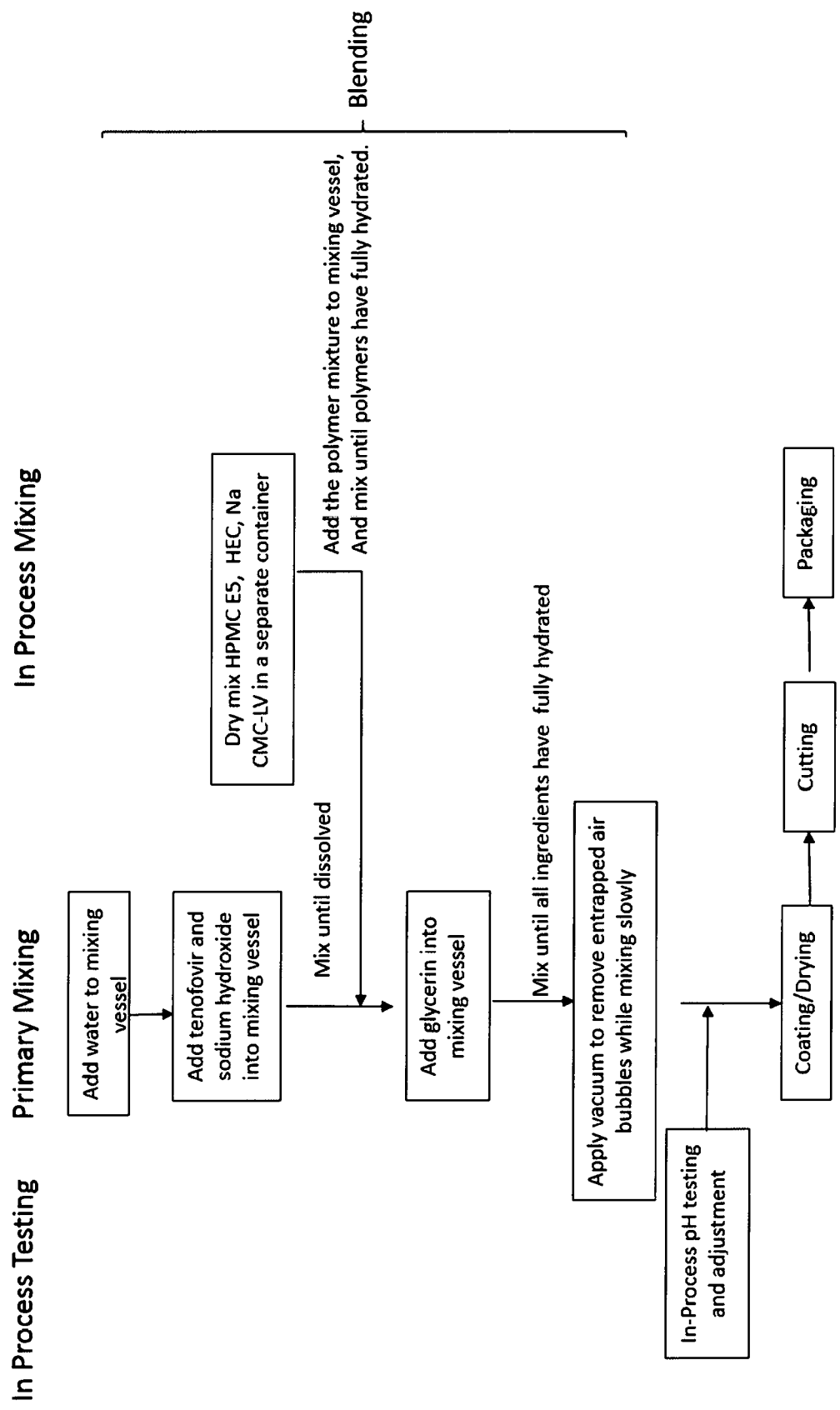
FIG. 3. A flowchart providing another aspect of a method as described herein.

In another non-limiting aspect, shown in FIG. 3, the protocol is suitable for large-scale production of films, and includes, under constant mixing, adding an alkalinizing/solubilizing agent, such as sodium hydroxide, and antiretroviral to a solvent, such as water, until dissolution. Separately, a dry mix of HPMC, HEC, and CMC is formed and then is added to the solution, mixing until the polymers are fully hydrated. Afterwards the plasticizer, for example glycerin, is added to the solution. Next, the solution is exposed to vacuum while under gentle mixing to remove any entrapped air bubbles. Lastly, the pH is tested and, if necessary, adjusted.

In aspects, a pre-film solution includes:

| Ingredient | Composition (%) |
| --- | --- |
| Active agent | 0.1-2 |
| Hydroxyethyl cellulose | 1.5-6-7 |
| Hydroxypropyl methylcellulose | 1.5-6-8 |
| Carboxymethylcellulose Sodium (Low Viscosity, USP) | 0.5-2-6 |
| Glycerin, USP | 0.5-2-4.4 |
| solubilizing/alkalinizing agent | 0-0.3-0.5 (to maintain desirable pH) |
| MilliQ to | 100 |

In other aspects, a pre-film solution includes:

| Ingredient | Concentration (%) for 40 mg per 2" × 2" film | Concentration (%) for 10 mg per 2" × 2" film |
| --- | --- | --- |
| Active agent | 2 | 0.5 |
| Hydroxyethyl cellulose (250 L Pharm) | 6 | 6 |
| Hydroxypropyl methylcellulose Methocel E5 | 6 | 6 |
| Carboxymethylcellulose Sodium (Low Viscosity, USP) | 2 | 2 |
| Glycerin, USP | 2 | 2 |
| solubilizing/alkalinizing agent | 0.28 | 0.07 |
| MilliQ to QS | 100 | 100 |

In a non-limiting aspect, the pre-film solution includes 6% wt. HEC, 6% wt. HPMC, 2% wt. NaCMC, 2% wt. glycerin, 0.5% wt. of an antiretroviral composition, 0.28% wt. sodium hydroxide, and pure water Q.S. In another non-limiting aspect, a pre-film solution includes 6% wt. HEC, 6% wt. HPMC, 2% wt. NaCMC, 2% wt. glycerin, 2% wt. of an antiretroviral composition, 0.07% wt. sodium hydroxide, and pure water Q.S.

While noted previously a desirable trait of the film is long-term stability for extended shelf-life, films that lack such long-term stability may nevertheless be desirable. In such aspects, a pre-film solution can include:

| Ingredients | Composition | |
|---|---|---|
| | Formulation | Formulation |
| Hydroxypropyl methylcellulose | 3 | 6 |
| Hydroxyethyl cellulose | — | 6 |
| PVP-K90 | — | 2 |
| Carboxymethylcellulose Sodium (Low Viscosity, USP) | 2 | — |
| Carboxymethylcellulose Sodium (Medium Viscosity, USP) | 2 | — |
| Active agent | 0.15-1 | 0.5-2 |
| solubilizing/alkalinizing agent | QS | QS |
| Glycerin | 2 | 2 |
| MilliQ QS to | 100 | 100 |

After the solution achieves a suitable pH, the solution is poured on an automatic thin film applicator for solvent casting. The applicator may be a heated surface. The solution is then dried. Suitable drying protocols can include a temperature of greater than 30° C., greater than 40° C., greater than 50° C., or greater than 60° C., all subranges therebetween inclusive. Drying time will depend on the temperature used, but can be in the range of 5-35 minutes, all subranges therebetween inclusive. In one non-limiting aspect, the solution is dried at about 71° C. for about 16 minutes. The produced film is then removed and cut to a suitable size, for example, 2 inches by 2 inches.

The film composition described herein dissolves in vivo, and may be administered for a period of time, or at intervals, ranging from as needed to hourly, daily, weekly, monthly, or yearly, including increments there between, such as from one to six times per day, daily, every other day, weekly, bi-weekly, monthly, bi-monthly, quarterly, etc. An appropriate dosing schedule can be determined by a person of ordinary skill, such as a physician.

EXAMPLES

Example 1

A consideration for preparation of a thin film dosage form is the film-forming polymer(s) that are used. The film-forming polymers could play a role in the properties and stability of the final dosage form, hence the choice of the polymers is a consideration. In this work, the initial screening was done using X-ray diffraction for selection of polymers and appropriate polymer:TFV ratio to keep TFV in a solubilized form. This approach resulted in several possible combinations of selected polymers based on which multiple placebo formulations were designed. TFV was loaded in selected placebo formulations. A suitable TFV formulation was identified based on TFV content of the film to achieve target dose and stability of the formulation. Based on this approach a TFV film formulation containing 40 mg TFV per film was successfully developed. The suitable TFV film formulation was comprehensively characterized for various physical, mechanical and biological properties. Finally, the formulation was subject to a short term accelerated stability testing.

Materials and Methods

Tenofovir (TFV) was supplied by Contraceptive Research and Development (CONRAD). The description of the polymers used and their vendors is provided below; sodium carboxymethylcellulose (NaCMC) low and medium viscosity (Spectrum Chemicals, New Brunswick, N.J., USA) hydroxypropyl methylcellulose (HPMC) (Methocel™ E5 Premium LV and K4M, DOW chemicals, Midland, Mich., USA), hydroxyethyl cellulose (HEC) (Natrosol 250 L Pharm, Ashland Polymers, Wilmington, Del., USA), polyvinyl pyrrolidone K-90 (Fluka, St. Louis, Mo., USA). All the other chemicals were purchased from Spectrum Chemicals.

X-ray diffraction (XRD) was used to study the solid state solubility of TFV in a series of polymers like HPMC-E5, HEC, and NaCMC-LV. TFV and polymers were dissolved together in milliQ water on a magnetic stirrer to achieve various polymer to TFV (P:T) ratios. pH was adjusted to 6-6.5 using sodium hydroxide equimolar to TFV. The solutions were then lyophilized using a Freezone 6 lyophilizer (Labconco, MO, USA). The powder obtained after lyophilization was scanned on a Philips X-ray diffractometer between 5-50° 2θ. A 37-minute scan was obtained. Similarly obtained XRD scans for lyophilized pure polymers and lyophilized TFV (pH 6-6.5) served as controls.

Development of Thin Films

A series of placebo formulations were developed based on the following XRD data (Tables 1A and 1B):

TABLE 1A

Prototype placebo formulations

| | Formulation Code (% wt. of polymer solution) | | | | | |
|---|---|---|---|---|---|---|
| Component | 1F1 | 1F2 | 1F3 | 1F4 | 1F5 | 1F6 |
| HEC | 3 | 0 | 3 | 3 | 3 | 3 |
| HPMC | 3 | 3 | 0 | 3 | 3 | 3 |
| NaCMC-LV | 3 | 3 | 3 | 0 | 2 | 1 |
| Glycerin | 2 | 2 | 2 | 2 | 2 | 2 |

TABLE 1B

Prototype placebo formulations

| | Formulation Code (% wt. of polymer solution) | | | | | |
|---|---|---|---|---|---|---|
| Component | 2F1 | 2F2 | 2F3 | 2F4 | 2F5 | 2F6 |
| HEC | 6 | 0 | 6 | 6 | 6 | 6 |
| HPMC | 6 | 6 | 0 | 6 | 6 | 6 |
| NaCMC-LV | 6 | 6 | 6 | 0 | 4 | 2 |
| Glycerin | 2 | 2 | 2 | 2 | 2 | 2 |

Accurately weighed amounts of the polymers were dissolved in milliQ water and mixed on an overhead mixer (Eurostar power control visc, IKA) at 50 rpm to achieve complete polymer dissolution. Glycerin was used as a plasticizer. The formulations were characterized for viscosity using a Brookfield's viscometer. TFV-loaded formulations were prepared in a similar manner (Table 2):

TABLE 2

TFV-loaded formulations

| | 1% TFV formulation | | | 2% TFV formulation | |
|---|---|---|---|---|---|
| Component | 1F4 | 1F5 | 1F6 | 2F4 | 2F6 |
| HEC | 3 | 3 | 3 | 6 | 6 |
| HPMC-E5 | 3 | 3 | 3 | 6 | 6 |
| NaCMC-LV | 2 | 1 | 2 | — | 2 |
| Glycerin | 2 | 2 | 2 | 2 | 2 |
| TFV | 1 | 1 | 1 | 2 | 2 |

TFV was loaded in formulations 1F4, 1F5 and 1F6 at 1% level and at 2% level in formulations 2F4 and 2F6 (Table 2, above). In the case of the TFV-containing formulations, the final pH was adjusted to 6-6.5 using sodium hydroxide. The TFV-containing polymer solution was poured on an automatic thin film applicator (4340, Elcometer, MI, USA). The solution was dried at 71° C. for 16 min. The polymer sheet was peeled off the applicator and cut into 2×2 inch film pieces using die cutter press (Tipmann Die Cutter, IN, USA). TFV in each individual film was extracted using solid phase extraction (SPE) and estimated by ultra-performance liquid chromatography; UPLC (Acquity, Waters Corporation, MA, USA). For SPE, an individual TFV containing film was dissolved in 40 ml milliQ water. 1 ml of the film solution was further diluted with equal volume of 2% formic acid. 1 ml of the diluted solution was loaded on previously activated SPE cartridge (Oasis MCX extraction cartridge, 1 cc (30 mg), Waters, USA). The residual polymer was washed by eluting the SPE cartridge with 1 ml 2% formic acid. TFV was extracted with 5% methanolic ammonium hydroxide solution. Extracted TFV was estimated after an appropriate dilution with milliQ water. Waters Acquity UPLC equipped with a TUV detector and Empower data processing software was used for UPLC analysis. TFV was detected at 260 nm. Separations were achieved by injecting 3 μL of solution on an Acquity UPLC BEH C18 column (1.7 m 2.1×50 mm, Waters) at ambient temperature. The flow rate was 0.3 ml/min. The mobile phase consisted of 90% phosphate buffer (10 mM $K_2HPO_4$ and 4 mM t-Butylammonium bisulfate) adjusted at pH 5.7, and 10% Methanol.

Characterization of TFV Films

Prototype formulations 2F4 and 2F6 (TFV loading at 2% level) were selected for further characterization.

Physical properties: Weight and thickness of the film was measured. Water content was determined using a Karl fisher autotitrator (890 Titrando, Metrohm, Fla., USA).

Mechanical properties: A TX-XT Plus texture analyzer (TA instruments, DE, USA) was used for mechanical characterization. The films were held between two clamps separated by 4.58 mm. The force required to break the film when the top clamp was pulled upwards vertically at 3 mm/sec was recorded. Tensile strength was calculated by formula:

Tensile strength(N/mm$^2$)=Force at break(N)/cross-sectional area(mm$^2$)

Toughness of the film was calculated from the area under force versus displacement curve. For puncture strength determination, the film was placed in the film holder. A puncture probe (spherical end: ⅛ inch diameter) was passed mechanically at 1 mm/sec through the center of the film holder's aperture. The puncture strength was calculated by the formula:

Puncture strength(N/mm)=Force at break(N)/Thickness of the film(mm)

In vitro release: In vitro release of TFV from the films was monitored using a USP 4 flow through apparatus (CE7 smart, Sotax Corporation, MA, USA). 1×PBS (100 ml, 37° C.) circulated at a flow rate of 16 ml/min was used as dissolution medium. Samples were analyzed for TFV amount by UPLC after appropriate dilutions with milliQ water.

Stress testing: Individually-packaged films were subjected to stress testing at 50° C. The films were observed by microscopy for presence of TFV crystals periodically over the course of one month. Additionally, the films were also scanned for presence of crystals using the previously described XRD method before and after stress testing.

Compatibility with lactobacilli: The compatibility with lactobacilli was assessed by a standard microbicide safety test. The TFV films were dissolved in 1.25 ml ACES buffer. This solution was mixed with 1.25 ml of lactobacilli suspension in 1×PBS (pH 7.4). The bacterial suspension containing dissolved film was incubated at 37° C. for 30 min. samples were taken before and after incubation was complete. Bacterial viability was determined by standard plate count. A sample was considered compatible with lactobacilli if the reduction in viability was <log 10. ACES buffer treated or untreated bacterial suspension served as controls for the experiments.

In vitro Anti-HIV activity of the TFV film was assessed by TZM-bl assay in vitro as well as in an excised cervical tissue model ex vivo. For TZM-bl assay, the TFV-containing and placebo films were dissolved in 4 ml of saline. Ten-fold serial dilutions were made in saline up to 1:107 of original solution. TFV drug substance dissolved in saline was used as control (original concentration-serial dilutions). Plated TZM-bl cells (1×10$^4$/well) were treated with 25 uL of respective dilutions for 2 h. HIV-1Bal was added next and the assay was cultured for 48 h. Infection was detected by adding BrightGlo (Promega) chemiluminescent developer of luciferase to each well. Control wells comprising cells alone or cells with HIV 1 only served as background and maximal luciferase activity, respectively. Efficacy was calculated as % Inhibition of infection by the formula:

% Inhibition=[(Treated Well-Cells alone)/(HIV-1only-Cells alone)]*100

In vitro toxicity of TFV film towards TZM-bl cells was evaluated by a standard 3-(4,5-dimethyl-thiazol-2-yl)-2,5-diphenyl tetrazolium bromide (MTT) assay. TZM-bl cells were treated with identical dilutions of film solution as used for the efficacy assay described above.

Stability Testing

TFV formulation 2F6 was scaled up for stability testing. The films were subjected to a 6-month accelerated stability protocol at 40° C./75% RH and stability samples were collected at 0, 3, and 6 months according to International Council for Harmonisation of Technical Requirements for Registration of Pharmaceuticals for Human Use (ICH) guidelines. In addition, the films were subjected to stress conditions at 50° C. for 3 months and the stability samples were collected at 0, 1, and 3 months. At each time point the weight and thickness of the film was measured. Other characterization parameters included analysis of TFV content, content uniformity, and in vitro release. Water content of the film was determined by a Karl Fisher autotitrator. Puncture strength test was used as measure of mechanical strength of the films. Additionally, in vitro compatibility of the films with lactobacilli was tested at each time point and ex vivo anti-HIV activity was evaluated at specific time points.

Statistics

Data was evaluated for statistical significance using analysis of variance (ANOVA). A difference of $p<0.05$ was considered statistically significant.

Results

Solid-State Solubility

TFV was dissolved along with various polymers to achieve P:T ratio 1, 3, or 6. The solutions were lyophilized and subjected to XRD analysis. Lyophilized TFV alone showed broad diffraction peaks at 2θ angles of 15.19-15.87 and 26.41, confirming that lyophilized TFV retained some crystallinity. Low intensity broad peaks were also observed at 9.38, 11.23, and 20.90 2θ angles (FIG. 1, top row). At P:T 1, none of the other polymers tested could convert TFV into complete amorphous form as the peaks associated with TFV (15.19-15.87 and 26.41) were still visible at that ratio (FIG. 1, column A). There was a slight shift in the peak positions and pattern for NaCMC:TFV. Broad doublet at 15.19-15.87 which is characteristic for TFV, disappeared and single peaks emerged at 6.56 and 13.06. This may suggest an interaction between TFV and NaCMC at a molecular level (FIG. 1, column A). The X-ray defractograms for HEC, HPMC, and NaCMC-LV at higher P:T ratio like 3:1 and 6:1 were devoid of any of the characteristic TFV peaks and displayed hollow patterns typical for an amorphous material (FIG. 1, columns B and C). This indicated that TFV was solubilized in amorphous polymer matrix. Thus, the XRD study suggested that polymers HPMC-E5, HEC, and NaCMC-LV were able to solubilize TFV when P:T ratio was adjusted to 3 or higher.

Development of Films

The formulation development was carried out in two steps. First, a series of prototype placebo formulations were developed (Tables 1A and 1B, above), and then TFV was loaded in selected formulations. The prototype formulations in Table 1A were designed to contain 1% TFV load while the prototypes in Table 1B were designed to contain 2% TFV load. The viscosity data generated for the prototype placebo formulations is presented in Tables 3A and 3B:

TABLE 3

A: Viscosity of the placebo formulations

| | Formulation Code | | | | |
|---|---|---|---|---|---|
| | 1F1 | 1F2 | 1F3 | 1F4 | 1F5 | 1F6 |
| Viscosity | UAH | UAH | UAH | A | UAH/MH | A |

B: Prototype placebo formulations

| | Formulation Code | | | | |
|---|---|---|---|---|---|
| | 2F1 | 2F2 | 2F3 | 2F4 | 2F5 | 2F6 |
| Viscosity | UAH | UAH | UAH | A | UAH | A |

Data presented as mean ± SD (n = 3)
UAH: unacceptably high;
UAH/MH: unacceptably high or moderate;
A: acceptable Formulations 1F1, 1F2, 1F3, 1F5, 2F1, 2F2, 2F3, and 2F5 had a viscosity which made them difficult to pour on the applicator. The high viscosity also resulted in entrapment of air in the solution. Hence these prototypes were not considered for TFV loading. In case of prototypes 1F4, 1F5, 1F6, 2F4, and 2F6 viscosity was low enough to facilitate easy pouring of the solution on the applicator. Air entrapment in these prototypes was also less (1F5, 1F6, and 2F6) or completely absent (1F4, 2F4). Prototypes 1F4, 1F5, 1F6, 2F4, and 2F6 were selected for TFV loading. TFV content in individual films belonging to various prototypes was determined (Table 4):

TABLE 4

TFV content in the prototype TFV formulation

| | Formulation Code | | | | |
|---|---|---|---|---|---|
| | 1F4 | 1F5 | 1F6 | 2F4 | 2F6 |
| TFV per film (mg) | ~20 | ~20 | ~20 | ~40 | ~40 |

Data presented as mean SD (n = 5)

Prototypes 1F4, 1F5, and 1F6 contained TFV ~20 mg per film. Prototypes 2F4 and 2F6 did contain ~40 mg of TFV. Since the target TFV dose for this particular project was 40 mg TFV per film, prototypes 2F4 and 2F6 were accepted for further characterization.

Characterization of Films

Both prototype formulations 2F4 and 2F6 produced easy to peel and soft films. The film matrix on 2F4 showed the presence of some cracks. The surface of formulation 2F6 appeared more uniform. Films belonging to 2F4 were thinner and lighter in weight compared to the films belonging to 2F6. The TFV release from both the formulations was rapid and comparable. Close to 100% of the entrapped TFV was released with 45 min. The 2F6 films had a higher puncture strength value compared to 2F4. Neither film had any toxic effects on the lactobacilli, and both retained anti-HIV activity in TZM-bl cells. However, 2F4 stressed at 50° C. started showing the presence of TFV crystals/black artifacts by day 29 of testing. No TFV crystals or black artifacts were visible in the stressed TFV formulation 2F6 during one month exposure at 50° C. XRD spectra of both films before the beginning of the stress testing showed no TFV peaks. XRD spectra recorded on 2F4 films after stress testing showed peaks characteristic for TFV. The films belonging to 2F6 retained amorphous nature even after stress testing. Since TFV formulation 2F6 showed superior stability compared with 2F4, 2F6 was chosen for the scale-up and short term accelerated stability testing.

Stability

The TFV films were smooth, soft, flexible and translucent in nature. Physical properties of the films measured on day zero are given in Table 5:

TABLE 5

Day zero characterization of TFV film
Physical properties of TFV films determined on Day zero

| Weight (mg) | 363.75 ± 41.35 |
|---|---|
| Thickness (μm) | 89.09 ± 13.75 |
| Water content (%) | 7.08 ± 0.81 |
| Puncture strength (N/mm) | 70.88 ± 20.25 |

The data is presented as mean ± SD (n = 5)

Figure 4:
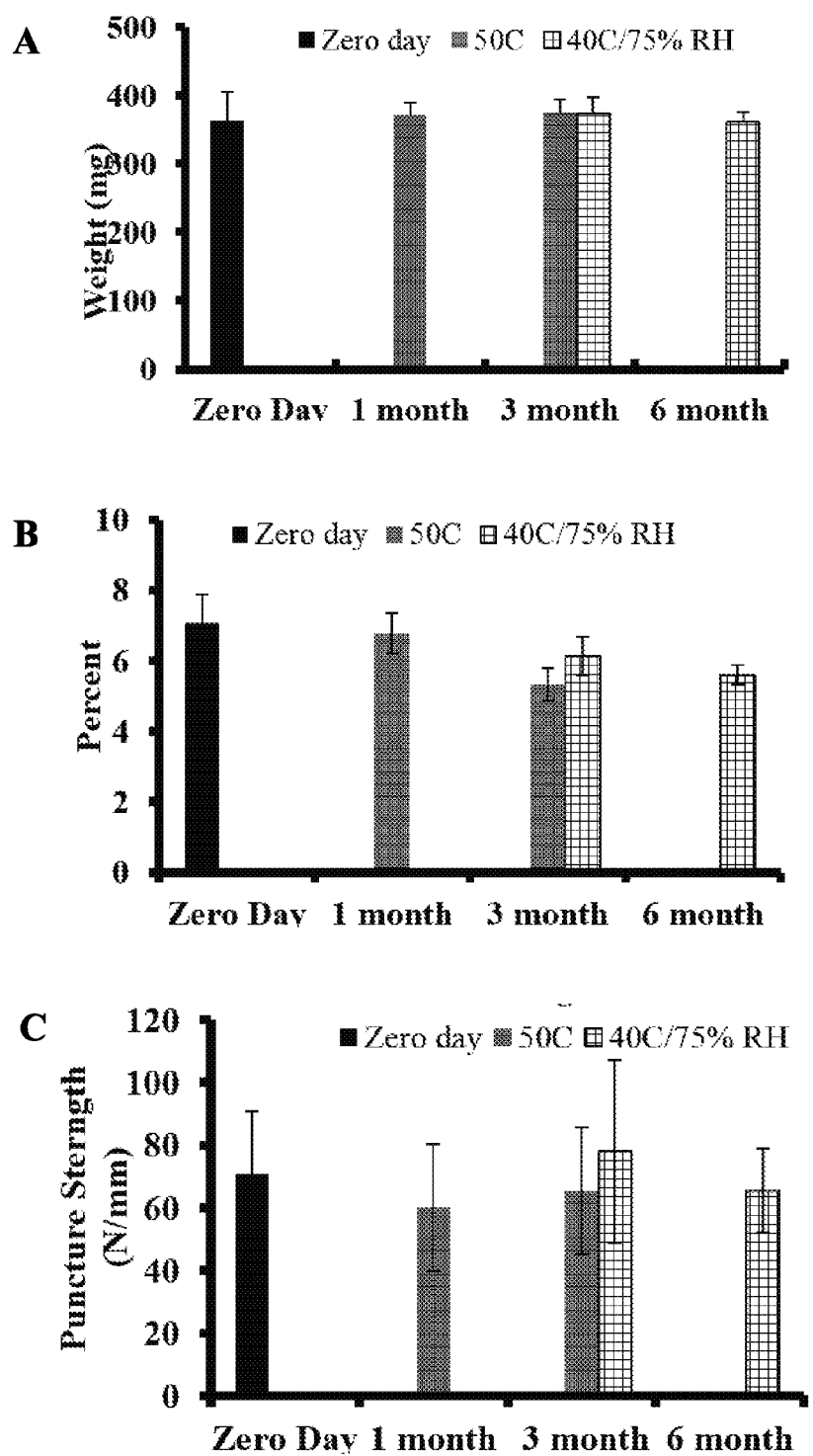
FIG. 4. Physical and mechanical properties of a TFV film, according to an aspect of a film described herein, placed on stability testing; A. Weight, B. Water content and C. Puncture strength. The weight of the films remained unchanged during the stability testing (n=1). Decline in the water content (n=3) and the variability in the puncture strength (n=3) was statistically not significant (p>0.05).
Figure 5:
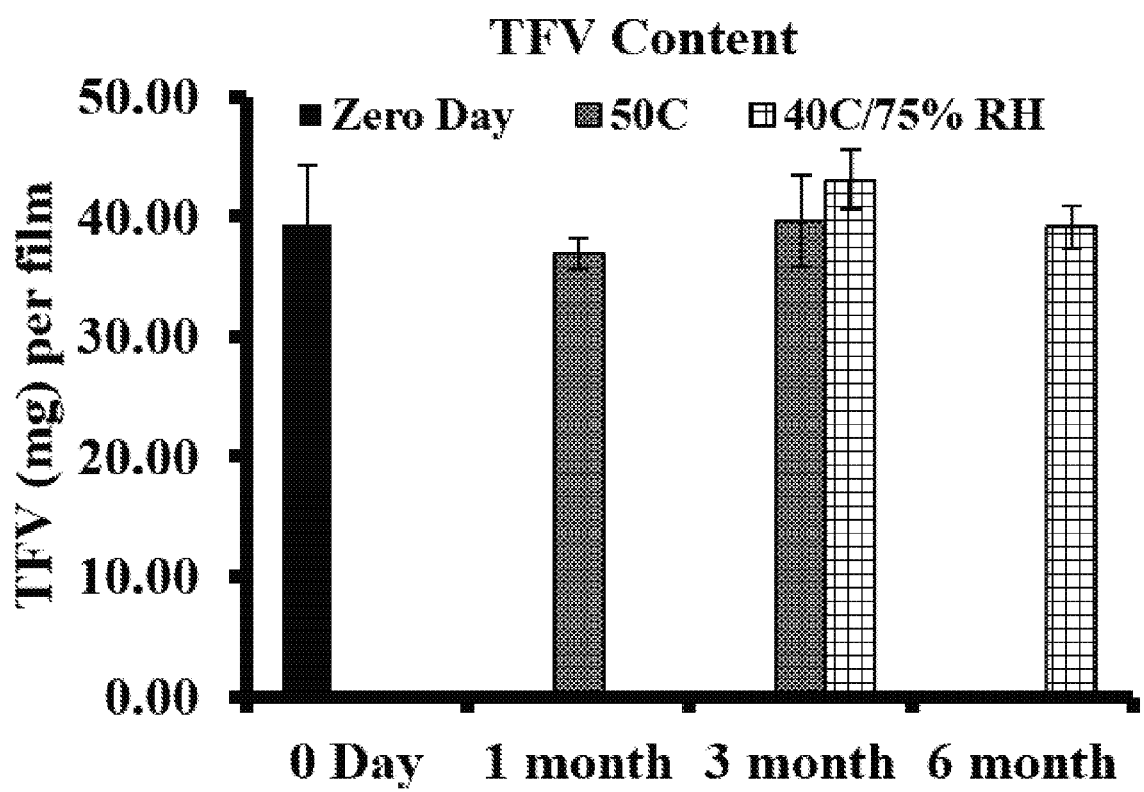
FIG. 5. TFV content in a film as described herein (n=5) remained within the acceptable limits (90-110%) throughout the stability testing.
Figure 6:
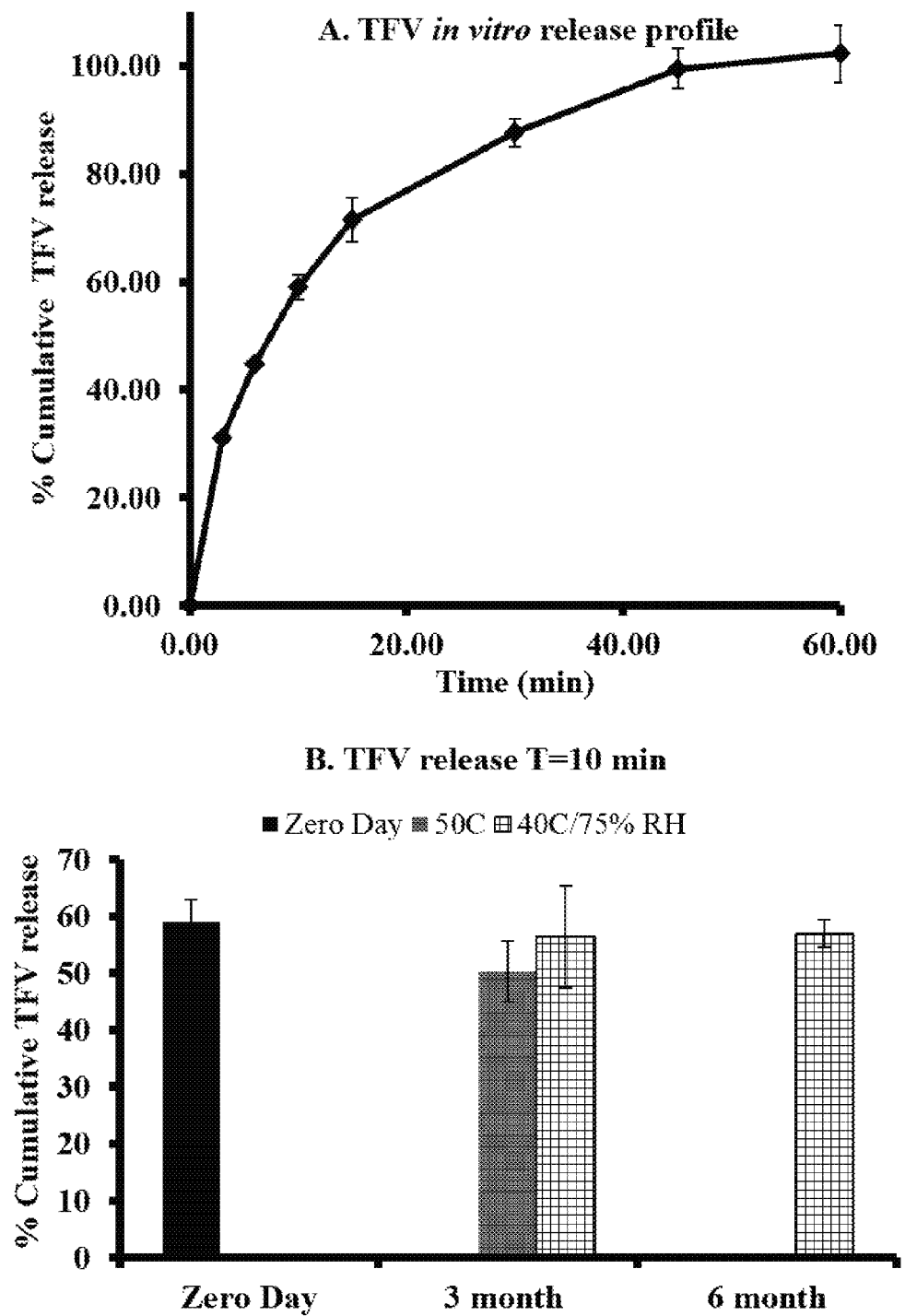
FIG. 6. Films according to aspects described herein released TFV rapidly in vitro (n=3). A. A representative dissolution profile B. TFV cumulative release at 10 minutes for films under stability conditions.

Weight of the films remained unchanged throughout the stability testing period (FIG. 4A). Variability observed in water content and puncture strength was statistically insignificant (p>0.05) (FIGS. 4B and 4C). Microscopy evaluation confirmed that TFV remained solubilized in the film polymer matrix at 50° C. for 3 months and at 40° C./75% RH for 6 months as no TFV crystals were observed at any time point at any of the two stability conditions. TFV dose of 39.27 mg TFV per film was achieved which was 10.79% w/w as calculated on a dry film weight basis. TFV content remained within the acceptable limit (90-110% of target dose) throughout the stability testing period (FIG. 5). Overall, almost 100% of the incorporated drug was released within 45 min (FIG. 6A). TFV release from the film was rapid and more than 55% of the incorporated TFV was released within first 10 min of the release test. The TFV release pattern remained unchanged in the films subjected to stability testing (FIG. 6B). The TFV films had an original water content of approximately 7%, which decreased slightly during the stability testing (p>0.05). TFV films showed excellent compatibility with various strains of lactobacilli (Table 6):

TABLE 6

Compatibility of TFV films with lactobacilli

| | | Log difference after 30 min incubation | | |
|---|---|---|---|---|
| | | 50° C. | 40° C./75% RH | |
| Strain | Day zero | 3 month | 3 month | 6 month |
| L. crispatus ATCC 33197 | −0.235 | 0.009 | 0.094 | −0.009 |
| L. jensenii ATCC 25258 | −0.138 | −0.035 | −0.038 | −0.086 |
| L. jensenii LBP 28Ab | −0.367 | −0.041 | −0.099 | −0.035 |

Discussion

The target for the above experiments was to develop a thin polymeric film formulation containing same amount of TFV as present in a single administration of TFV gel formulation (i.e. 40 mg of TFV per film). The use of solubilizers like surfactants and co-solvents to achieve target TFV dose was intentionally avoided in this work due to published reports relating increases in viral infectivity in vaginal tissue with commonly used solubilizing components. Instead, an approach to identify a polymer matrix in which TFV has enough solubility was taken. Another selection criterion for the polymer matrix was the amenability for convenient processing during the manufacturing operation.

HPMC-E5, HEC, and NaCMC-LV were selected as film-forming polymers due to their acceptable regulatory status. XRD was used to determine the solid-state solubility of TFV in each of these individual polymers. XRD data clearly suggested that the individual polymer to TFV ratio should be adjusted to 3 or higher to achieve TFV solubility in any of these individual polymers. Based on this observation, a series of prototype placebo formulations were developed. Since at this stage it was not known what TFV loading was required to achieve 40 mg TFV dose per film, TFV at 1 and 2% level were utilized as starting points. For each TFV loading level a separate panel of prototype placebo formulations was developed (Tables 1A and 1B, above). Table 1A represents the prototype placebo formulations developed for 1% TFV loading. Prototypes 1F1, 1F2, 1F3, and 1F4 abided by the observation from XRD data in the sense that at 1% TFV loading individual polymer to TFV would be adjusted to 3. However 1F1, 1F2, and 1F3 produced highly viscous polymer solutions containing plenty of air bubbles. These highly viscous solutions presented great difficulty in pouring the solutions on the film applicator. Since prototype 1F4, which was devoid of NaCMC-LV, showed significantly lower viscosity, NaCMC-LV was considered a viscosity determining factor in these formulations. Reducing NaCMC-LV to lower concentrations in 1F5 and 1F6 significantly reduced viscosity. Prototypes 1F4, 1F5, and 1F6 were easy to pour and had fewer or no air bubbles. However, the reduction in the levels of NaCMC-LV meant that NaCMC-LV to TFV ratio was lower than 3, assuming the TFV loading would be at 1%. The polymer to TFV ratio of 3 was maintained in the case of HPMC-E5 and HEC in all the prototype formulations. Since the ultimate aim was to achieve TFV solubility in total polymer matrix and not in an individual polymer, and since two of the three polymers in the formulation were maintained at XRD-data suggested levels to achieve TFV solubility, it was decided to proceed further with 1% TFV loading in 1F4, 1F5, and 1F6 at this stage. A similar logic was applied behind development of 2F5 and 2F6 at reduced NaCMC-LV level. Formulations 2F4 and 2F6 were selected for TFV loading at 2% level. TFV loading levels directly influenced the final TFV dose per film. TFV loading at 2% resulted in ~40 mg TFV per film whereas TFV loading at 1% resulted in ~20 TFV dose per film. TFV containing formulations 2F4 and 2F6 containing ~40 mg TFV film per film were selected for further characterization. Formulations 2F4 and 2F6 had comparable TFV content and TFV release from both the formulations was rapid. Formulation 2F6 had higher puncture strength that 2F4. Very high puncture strength may indicate brittleness. Formulations 2F6, however, was flexible and did not break on folding which indicated that even though the puncture strength of 2F6 was higher than 2F4, it was not high enough to make the films brittle. TFV loaded formulations 2F4 and 2F6 were stressed at 50° C., 10° C. higher than ICH accelerated conditions of 40° C./75% RH. The microscopy and XRD of 50° C. stressed 2F4 showed presence of TFV crystals. No such crystals were observed in stressed 2F6 films.

Since HEC and HPMC-E5 were the common components of the polymer matrix used in both the formulations, the superior stability of 2F6 may be attributed to presence of NaCMC-LV in that formulation. HPMC and HEC are non-ionic polymers. NaCMC, on the other hand, is ionized into —Na$^+$ and COO$^-$ species close to neutral pH. Phosphate groups of TFV (pKa 2.1 and 4.3) should acquire a negative charge at pH 6.5 whereas the primary amine group (pKa 7.3) on the heterocyclic ring should be positively charged (FIG. 1). An electrostatic association between ionized forms of NaCMC and TFV may reduce cohesive affinity of TFV molecules for each other and result in the stabilization effect observed in F3. In fact, the XRD data hinted at some interaction between TFV and NaCMC and a shift in 2θ peaks characteristic for TFV was observed in XRD pattern (FIG. 1). Mechanical properties of the placebo films also suggested a tighter network of polymer chains for 2F6 compared to 2F4 which may have played a role in retarding molecular diffusion of solute molecules. Because of its superior profile to resist crystallization under stress TFV loaded 2F6 was selected as optimal formulation for full characterization and stability testing.

A TFV-loaded formulation (2F6) was scaled up for a short-term stability study at ICH accelerated condition. One arm was subjected for stress testing at 50° C. TFV film stability was monitored using microscopy for development of TFV crystals in the film. Although this formulation was stressed for 1 month at 50° C. at the product selection and optimization stage, more rigorous testing based on ICH stability testing guidelines was needed before the product is accepted as a candidate for further development (like long term stability, cGMP manufacture for clinical trials etc.). In that context, absence of TFV crystallization throughout the stability testing was highly encouraging. The physical and mechanical properties of the films were satisfactory. The mechanical strength of the film is an important characterization criterion. Ideally, a vaginal film has enough flexibility to prevent a break during use. Films with higher flexibility may not remain flat or may roll. A hard film may result in vaginal irritation. There is no standard acceptability criterion for mechanical properties of vaginal films. Hence the mechanical properties are usually used for the purpose of quality control only. TFV films produced in this work remained soft, smooth, and flexible throughout the stability testing despite some variability in the puncture strength values which in any case was not statistically significant.

Water content could significantly impact stability of film formulations. This especially holds true for the films carrying high drug load. The presence of moisture inside the films would increase the molecular movements of the incorporated drug molecule thus facilitating eventual crystallization. Ideally the water content is as low as possible. It could be concluded that the water content in TFV film was low enough not to affect the stability and induce crystallization. A targeted TFV dose of 40 mg TFV per film was achieved which remained unchanged during stability testing. As maintained earlier, the purpose of TFV film is the vaginal delivery of TFV for protection from HIV infection. Usually in coital action dependent products like vaginal films and gel, the time gap between administration of the product and HIV entry is small as the user tends to administer the product very close to coitus. This also narrows the window available for the active agent to reach its site of action. Thus, it is very important that the active agent is released rapidly from a coitally-dependent product. TFV release from the film was very rapid. Approximately 55% of the incorporated TFV was released within 10 min. Compatibility of TFV films with innate vaginal lactobacilli flora was also established during the stability testing.

Example 2

The current Example describes a Phase 1 trial of an antiretroviral film as described herein. The safety, acceptability, pharmacokinetics, and pharmacodynamics were compared between TFV 1% gel, two doses of TFV film, and placebo.

Materials and Methods

This was a Phase 1, five arm, single-site, double blind, randomized placebo-controlled trial comparing the safety and acceptability of TFV 1% gel and two doses of TFV film to placebo. The protocol was approved by the University of Pittsburgh Institutional Review Board.

The sample size was based on the exact binomial probability of observing at least 2 adverse events. For a given arm, if the true rate of a given toxicity endpoint is 5%, 14 women per arm provide 85% power to exclude toxicity endpoint rates greater than 30%. Fourteen women per arm assured that a 95% confidence interval for the difference between the placebo and TFV toxicity rates has an upper limit no more than 16% when the observed toxicity rates for placebo and active gel are both 5%. Participants were replaced if they reported missing two or more home doses or if the dose on the day prior to the biopsy visit was missed.

Seventy-eight HIV-uninfected women were enrolled between January and December 2014; women were recruited from gynecology clinics at Magee-Womens Hospital of the University of Pittsburgh Medical Center and the surrounding community. All participants provided written informed consent for screening and study procedures. Participants were 18-45 years of age and agreed to be sexually abstinent from 7 days prior to study product use through 7 days after study product use. Exclusion criteria included pregnancy, hysterectomy, abnormal complete blood count or complete metabolic panel, anticipated vaginal bleeding during the first week after enrollment, and the use of antibiotics or antifungals in the 7 days preceding enrollment.

Women were randomized with equal frequency to one of five arms using a permuted block design with block sizes of 5 and 10. The groups included 4 mL universal placebo gel (HEC gel), 4 mL TFV 1% gel, placebo film, TFV (10 mg) film, and TFV (40 mg) film. The TFV film was formulated in a cellulose based vaginal film containing HPMC, HEC, NaCMC, and glycerin, as described herein.

The primary objective was to assess safety; the primary endpoints were grade 2 or higher adverse events deemed related to study product. Secondary objectives included the impact of product on vaginal microbiota and TFV concentrations in plasma, vaginal fluid, and cervicovaginal lavage (CVL), as well as TFV-DP concentrations in genital tissues. For the pharmacokinetic (PK) analyses and the exploratory objective using an ex vivo challenge assay as a pharmacodynamic (PD) measure, only the 71 women who were deemed evaluable and had no evidence of study product misuse at the time of biopsies were included. Evaluable participants were those who reported using their product at home for 5 out of 6 doses including the day prior to the biopsy visit.

There were four study visits in total. Eligibility was initially assessed at the screening visit. In addition, a baseline 10 mL CVL was obtained using normal saline. Eligible participants then presented for enrollment within 56 days. After baseline samples, including microbiota, were collected, participants self-inserted the first dose of study product while still in the clinic. Participants were counseled on product use and shown diagrams to clarify the insertion process. Women in the gel group were instructed to insert the applicator into the vagina and push the plunger to expel gel. Women randomized to film were instructed to fold the 2×2 film in half, drape the film over a finger, and insert the film without an applicator. Site staff was readily available for assistance. Participants were provided with five additional doses of study product to use daily at home. One to three days after the enrollment visit, participants were contacted by telephone to inquire about challenges with study product use and whether they experienced any Adverse Events (AEs). One week after enrollment, participants presented for the third clinic visit (V3) at which point they had plasma collected and then inserted the last dose of study product in the clinic. Two hours later, participants underwent specimen collection, including plasma, CVL and genital tissue biopsies (two cervical and two vaginal). Prior to collecting the genital biopsies, a large cotton swab was used to remove any visible gel or film from the biopsy site. The 2 hour time point was timed to mimic peri-coital use. Participants returned for a final safety visit (V4) one month after enrollment and a CVL was collected.

Local and systemic safety was assessed by eliciting AEs through history, physical exam, and laboratory evaluation. AEs were defined and graded according to the Division of AIDS Table for Grading Severity of Adult and Pediatric AEs, Version 1.0, December 2004 and the Female Genital Grading Table for Use in Microbicide Studies (Addendum 1 to the DAIDS Table for Grading Adult and Pediatric Adverse Events, Version 1.0, December 2004). The number of AEs by body system and relationship to study product was tabulated; individual participants contributed only once to the calculation of event rates. The proportion of participants experiencing grade 2 and higher AEs deemed related to study product was compared across treatment arms using Fisher's exact tests. To evaluate the effects of gel and film formulations of TFV on vaginal microbiota, Nugent scores and quantitative vaginal cultures and quantitative polymerase chain reaction (PCR) tests for selected microbes were compared between groups using Fisher's exact and Kruskal-Wallis tests. Participant opinions on product and acceptability were collected via self-administered questionnaires at the end of the biopsy visit (V3) and compared using Fisher's exact tests. Participant demographic and behavioral characteristics were compared across study arms using one way analysis of variance and Fisher's exact tests.

One set of tissue biopsies intended for quantitative drug analysis was washed, weighed, snap frozen, and stored at −80° C. prior to drug quantification. Concentrations of TFV and the metabolite TFV-DP were determined using either calibrators prepared in plasma or water, respectively. Quality controls were matrix-specific, and following homogenization and specimen preparation, the lower limits of quantification (LLOQ) of TFV and TFV-DP were 0.05 ng/sample and 50 fmol/sample, respectively. The LLOQ for TFV in plasma and CVL were 0.31 ng/mL and 5 ng/mL, respectively. For samples that were below the LLOQ of TFV and TFV-DP, the concentration was assumed to be half the LLOQ for plasma, CVL, cervicovaginal and rectal fluid samples and half the LLOQ adjusted for average weight of the cervical and vaginal tissue samples.

The second set of biopsies was used fresh for the ex vivo challenge assay. As previously described, the tissue biopsies were briefly exposed to HIV-1$_{BaL}$ in the laboratory and cultured to assess viral replication in the supernatant using HIV-1 p24 ELISA (Alliance, Perkin Elmer). A log-log, linear least-squared model with a subject covariate was used to test for the significance of the slope estimate, difference from zero, where a statistically significant negative slope indicated drug mediated virus suppression in the ex vivo challenge assay. For CVL PD activity, the assessment was performed in an in vitro TZM-bl assay with the CVL diluted to a final concentration of 1:5. The linear association between PD activity and TFV concentration in the CVL was assessed using Pearson's correlation coefficient.

Results

One hundred and fifty-five women were screened, and 78 women enrolled. Fifteen women were randomized to 10 mg TFV film, sixteen women to 40 mg TFV film, sixteen women to placebo film, sixteen women to TFV 1% gel and fifteen women to placebo gel. Three participants were deemed unevaluable: two participants did not use the product for the minimum requirement, and one participant was unable to keep her biopsy visit because of a family emergency. These three participants were replaced. Four additional participants were included in the safety evaluation but were not included in the exploratory outcomes (2 gel and 2 film users) because of product placement issues. At the time of the biopsy, the two women randomized to film were noted to have film distal to the vaginal introitus and the two women randomized to gel had no evidence of gel in the vagina. Of 234 scheduled clinic visits, 233 (99.6%) were completed. No differences with respect to demographic characteristics and sexual behavior were noted between study arms (Table 7):

TABLE 7

Demographic and Behavioral Characteristics of the Study Population

| Characteristic | Gel Placebo n = 15 | Gel Tenofovir 40 mg n = 16 | Film Placebo n = 16 | Film Tenofovir 10 mg n = 15 | Film Tenofovir 40 mg n = 16 | Total N = 78 | P-value |
|---|---|---|---|---|---|---|---|
| Race, n (%) | | | | | | | 0.89* |
| White, non-Hispanic | 12 (80%) | 12 (75%) | 11 (69%) | 12 (80%) | 10 (62%) | 57 (73%) | |
| Black, non-Hispanic | 2 (13%) | 3 (19%) | 4 (25%) | 2 (13%) | 5 (31%) | 16 (21%) | |
| Black, Hispanic | 0 | 0 | 0 | 1 (7%) | 0 | 1 (1%) | |
| Asian | 1 (7%) | 0 | 1 (6%) | 0 | 1 (6%) | 3 (4%) | |
| Bi-racial | 0 | 1 (6%) | 0 | 0 | 0 | 1 (1%) | |
| Age, years (SD) | 27.1 (7.5) | 29.5 (5.7) | 27.4 (6.1) | 25.6 (5.4) | 28.9 (5.0) | 27.7 (6.0) | 0.40† |
| Body Mass Index, kg/m² (SD) | 25.4 (3.5) | 25.8 4.4) | 28.5 (7.5) | 29.7 (9.0) | 28.9 (9.0) | 27.7 (7.1) | 0.34† |
| Education | | | | | | | 0.49* |
| High school graduate or less | 0 | 1 (6%) | 3 (19%) | 2 (13%) | 2 (12%) | 8 (10%) | |
| Some college or college graduate | 11 (73%) | 8 (50%) | 5 (31%) | 8 (53%) | 9 (56%) | 41 (53%) | |
| At least some post-graduate education | 4 (27%) | 7 (44%) | 8 (50%) | 5 (33%) | 5 (31%) | 29 (33%) | |
| Unmarried | 9 (60%) | 8 (50%) | 10 (62%) | 12 (80%) | 7 (44%) | 46 (59%) | 0.30* |
| Current Smoker | 2 (13%) | 4 (25%) | 2 (12%) | 3 (20%) | 2 (12%) | 13 (17%) | 0.82* |
| At least one prior pregnancy | 4 (27%) | 6 (38%) | 7 (44%) | 5 (33%) | 8 (50%) | 30 (38%) | 0.74* |
| Sexually active past 30 days, with male partner | 9 (60%) | 10 (62%) | 8 (50%) | 9 (60%) | 7 (44%) | 43 (55%) | 0.81* |

*P-value from Fisher's exact test
†P-value from one-way analysis of variance

Ninety percent of participants reported at least 1 AE during the course of study follow-up (FIG. 7). There were a total of 144 AEs reported, including 1 grade 2 related AE of vaginal pain occurring in the TFV gel group felt to be due to retained vaginal applicator caps. This particular participant missed several doses of study product, did not undergo biopsy procedures and was deemed non-evaluable. A pelvic exam performed when the participant presents for an interim visit with a complaint of pelvic pain revealed the presence of two applicator caps retained within the vagina, though no evidence of epithelial disruption. The participant had neglected to remove the cap from the applicator prior to self-insertion of gel product, resulting in displacement of the applicator cap into the vagina when the plunger was pressed.

Most AEs were grade 1 (91%). The most commonly reported AE was product leakage, which was more commonly reported in the gel group. There was a similar distribution of mild and moderate events across the five groups (FIG. 7). Based on cultivation and PCR-based methods, neither gel nor film impacted the microbiota over time, nor was there a shift in the Nugent Gram stain pattern associated with product use (data not shown).

Participants randomized to use the 40 mg TFV film and TFV 1% gel had plasma TFV concentrations after 7 doses [median, range] of 1.84 ng/mL (0.16, 5.45) and 0.86 ng/mL (0.16, 3.46), respectively (Table 8):

TABLE 8

Median TFV concentrations in biologic matrices

| | 1% TFV Gel n = 13 | 40 mg Film n = 15 | P-value[a] | 10 mg Film n = 14 | P-value[b] |
|---|---|---|---|---|---|
| Tenofovir (ng/mL) | | | | | |
| Plasma TFV after 6 doses | 0.86 (0.16, 3.46) | 1.84 (0.16 5.45)[a] | 0.17 | 0.40 (0.16, 2.81)[a] | 0.007 |
| Plasma TFV 2 hrs after 7th dose | 2.34 (0.16, 13.00) | 2.74 (0.16, 9.78)[a] | 0.96 | 0.98 (0.16, 2.27) | 0.007 |
| Rectal fluid TFV 2 hrs after 7th dose | 33.67 (1.65, 3689) | 33.99 (2.76, 1933) | 0.75 | 14 90 (0.73, 267) | 0.17 |
| Cervicovaginal lavage | $193 \times 10^3$ ($55 \times 10^3$, $1530 \times 10^3$) | $181 \times 10^3$ ($46.2 \times 10^3$, $653 \times 10^3$) | 0.39 | $72.5 \times 10^3$ ($30.4 \times 10^3$, $274 \times 10^3$) | 0.001 |
| Cervicovaginal fluid TFV after 6 doses | 531.97 (170.91, 819.53) | 1044 (2.08, 3996) | 0.052 | 337.58 (12.44, 2751) | 0.16 |
| Cervicovaginal fluid TFV 2 hrs after 7th dose | $2.85 \times 10^3$ ($1.20 \times 10^3$, $4.30 \times 10^3$) | $8.15 \times 10^3$ ($1.34 \times 10^3$, $15.76 \times 10^3$) | <0.001 | $1.63 \times 10^3$ ($0.16 \times 10^3$, $4.06 \times 10^3$) | <0.001 |
| TFV-DP levels (fmol/sample) | | | | | |
| Cervical tissue | 497 (72, 6461) | 2096 (9, 18817) | 0.27 | 78 (7, 1312) | 0.001 |
| Vaginal tissue | 662 (100, 4729) | 539 (7, 19344) | 0.44 | 112 (7, 2638) | 0.046 |

Data presented as median (range). Women who had poor product placement were excluded.
This included one woman randomized to the 40 mg film with visible film external to the vaginal introitus at the time of biopsy and two women randomized to tenofovir gel with no visible product in the vagina at the time of biopsies.
[a]P-value from Mann-Whitney U test for difference between 40 mg TFV film and 1% TFV gel
[b]P-value from Mann-Whitney U test for difference between 40 mg TFV film and 10 mg TFV film All participants randomized to active product had low plasma concentrations, though the 10 mg film group had significantly lower plasma concentrations relative to women randomized to the higher tenofovir dose groups (p=0.007). Tissue concentrations of TFV-DP in genital tissues were also comparable between the 40 mg TFV film and TFV 1% gel users, with women receiving the 10 mg TFV film having lower levels (p<0.00700705) (Table 8, above).

Figure 8A:
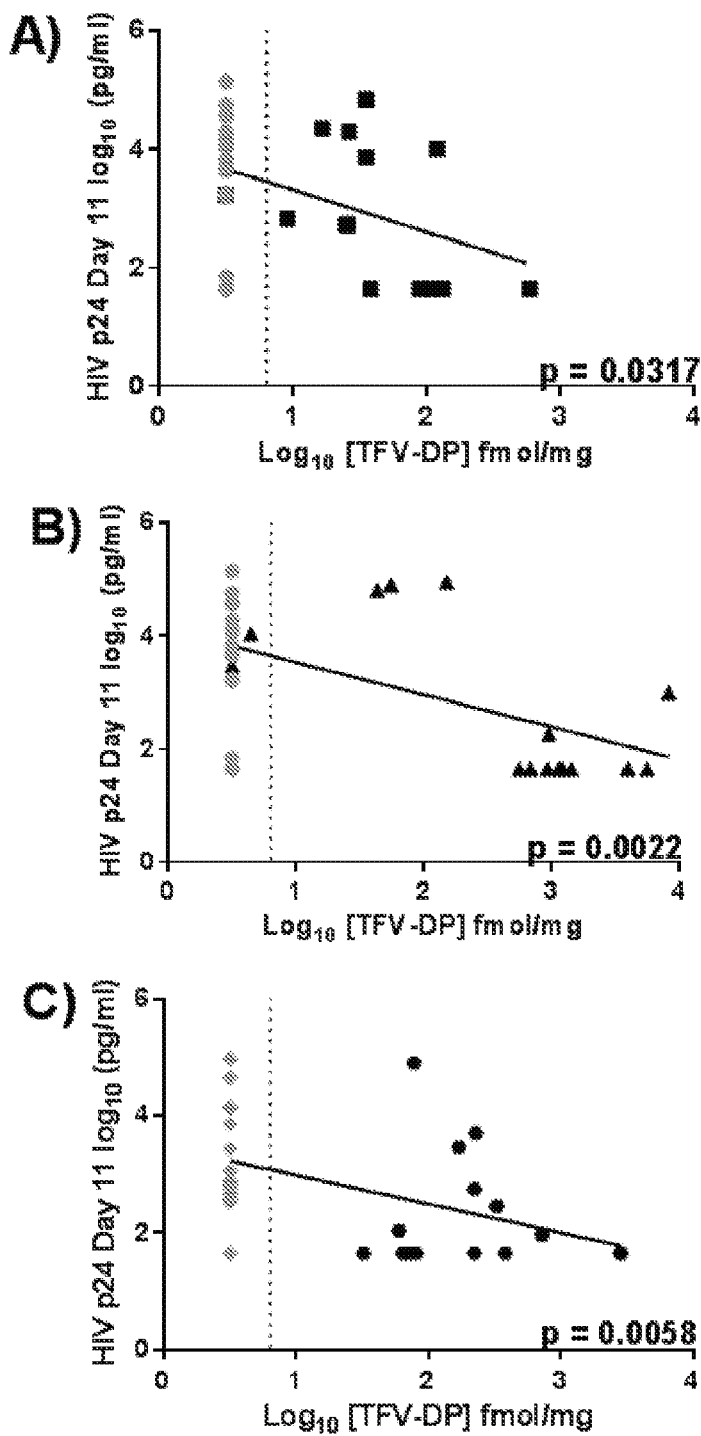
FIG. 8A-8B. Pharmacokinetic and pharmacodynamic correlations between tissue tenofovir diphosphate (TFV-DP) concentrations and capacity to replicate HIV in cervical and vaginal tissue. TFV-DP concentrations in cervical tissue (8A, panels A-C) correlated with significantly lower HIV-1 replication. Vaginal tissue (8B, panels D-F) did not demonstrate the same correlations. A and D) grey circle; placebo film, black square; 10 mg TFV film; B and E) grey circle; placebo film, black triangle; 40 mg TFV film; and C and F) grey diamond; placebo gel, black circle; TFV gel.
Figure 8B:
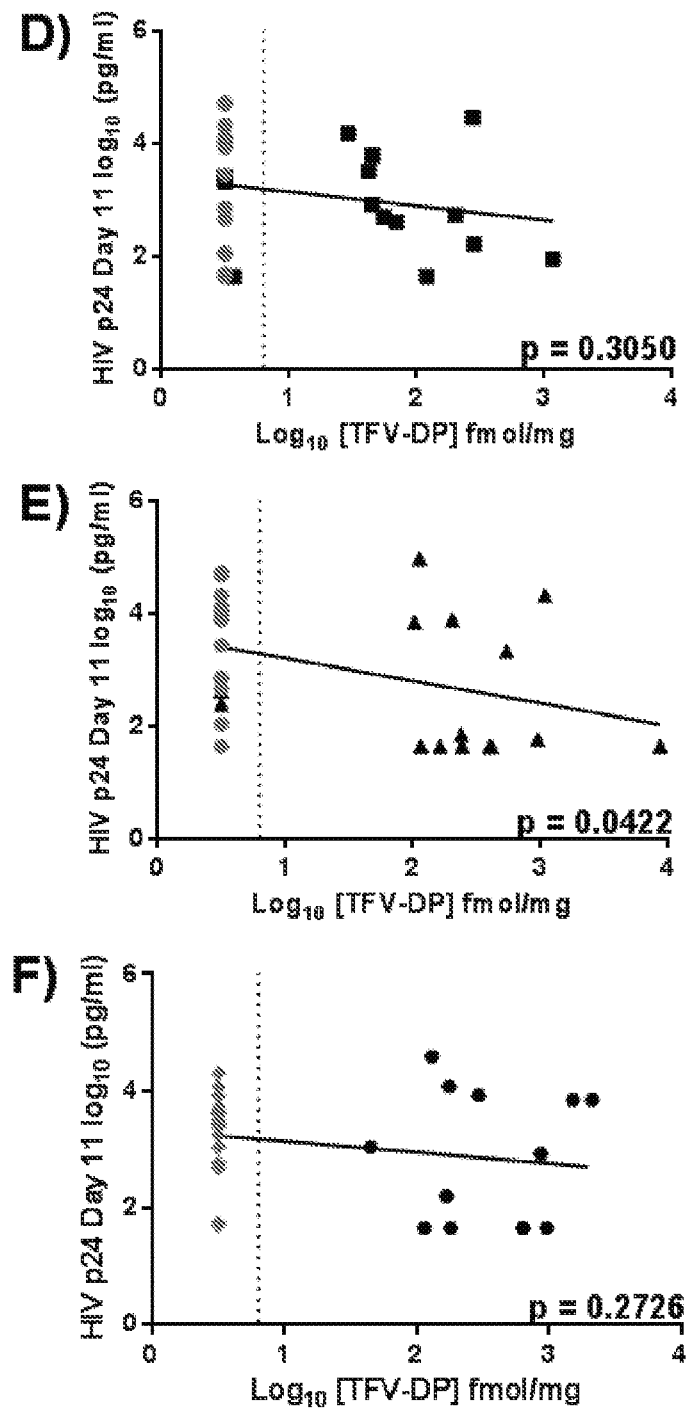
Figure 9:
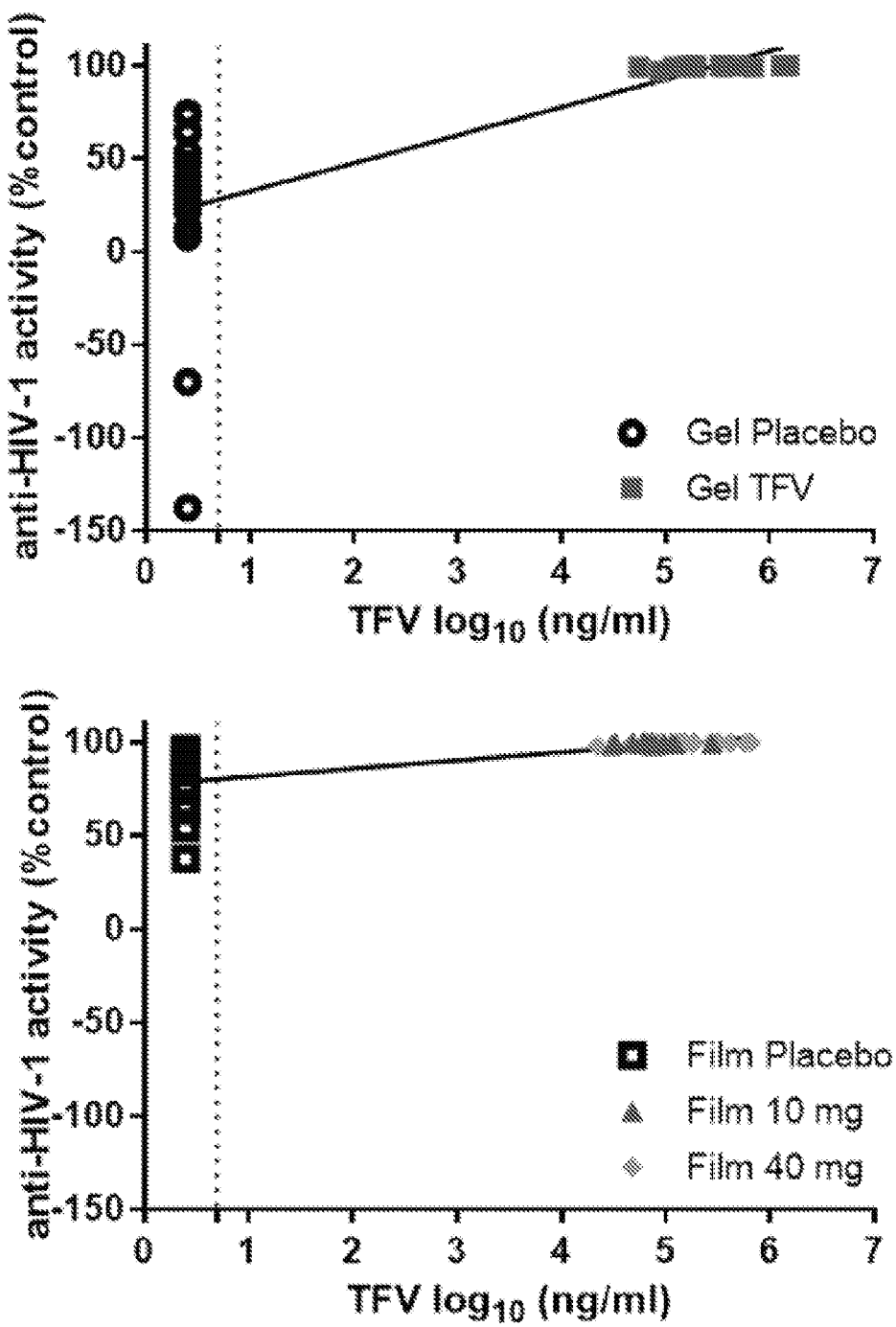
FIG. 9. HIV inhibitory activity in cervicovaginal lavage (CVL). CVL was collected from participants 2 hours after their last close. Tenofovir (TFV) was quantified and found to be >1000 ng/ml; placebo users had no detectable TFV and TFV at the ½ the lower limit of quantification (vertical dotted line) was determined was used. Gel users (upper panel) and film users (lower panel) showed significant anti-HIV activity (p<0.0001) with r=0.48 and 0.51, respectively.

When assessed for the potential to inhibit HIV infection, the three active products protected cervical tissues (FIG. 8A, panels A-C), but were less effective in vaginal tissue. Only the 40 mg TFV film demonstrated protection (FIG. 8B, panels D-F). CVL tested during product use showed significant anti-HIV activity when comparing products containing TFV to placebo (FIG. 9).

Figure 10:
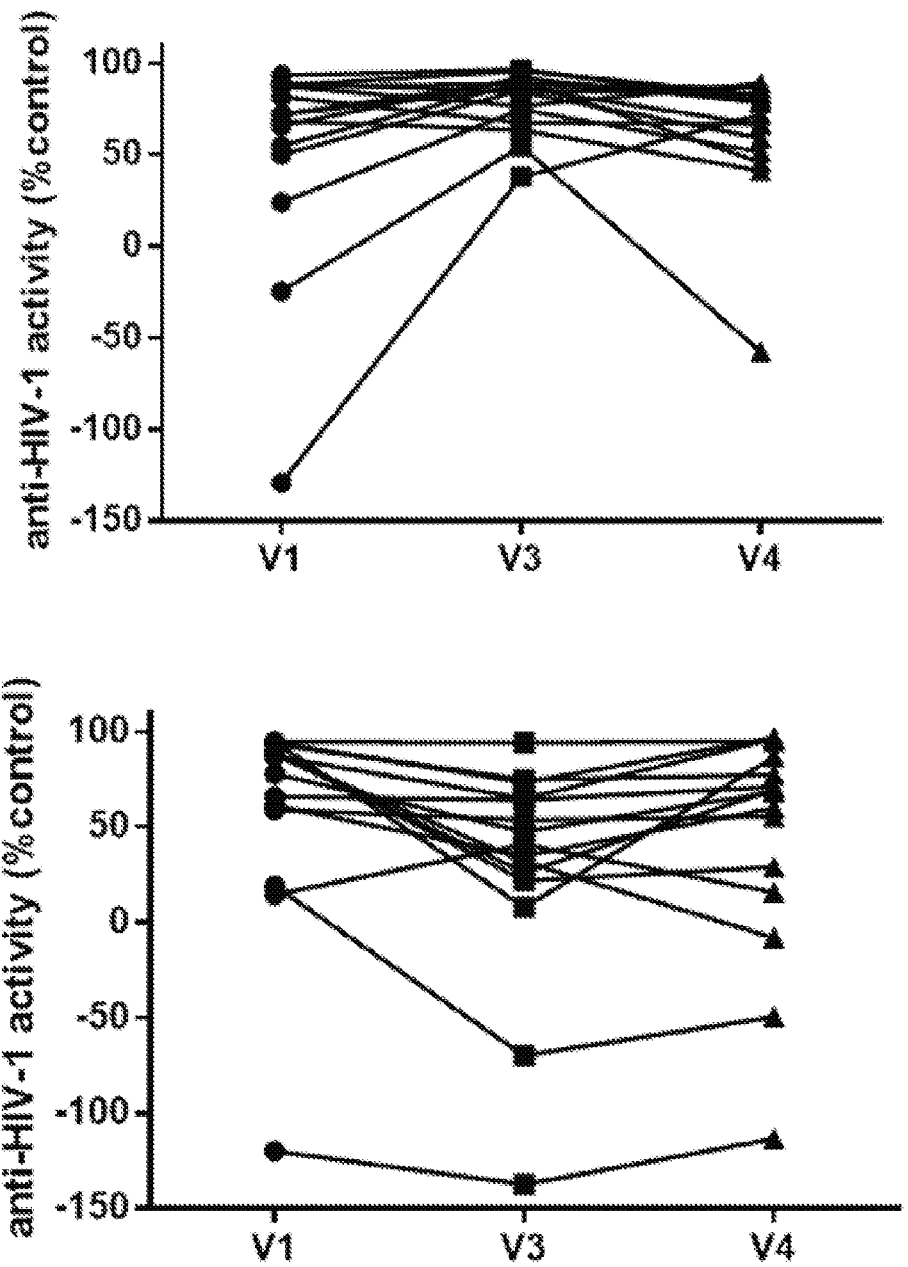
FIG. 10. Innate cervicovaginal lavage (CVL) anti-HIV activity. No significant difference in innate anti-HIV activity was found in CVL collected from placebo film users upper panel) or placebo gel users (lower panel) over time.

Because products inserted into the vagina could impact innate anti-HIV activity, changes in innate activity were evaluated over time and compared between gel and film placebo users (FIG. 10). No differences were noted during product use (visit 3) as compared to baseline (visit 1) or post-product use (visit 4).

Overall, study participants reported that both film and gel formulations were acceptable (Table 8, above). Seventy-two percent of film users and 77% of gel users reported that they would likely use the product should it be found effective against HIV. Participants' assessments of ease of use differed between formulation types, but not within each formulation group. For example, less than 10% of participants randomized to the gel groups described the insertion process as "difficult," 7% in the placebo group and 6% in the tenofovir group. In contrast, 49% of participants in the film groups reported that the product was difficult to insert (44% for placebo, 50% for the 40 mg film, and 53% for the 10 mg film). Of note, 72% of the film users reported that the product was easier to use with subsequent doses. More women randomized to the gel group described the product as "uncomfortable" once inserted (42% vs 19%). Gel users reported more product leakage (100%) compared to the film group (66%).

Discussion

In this first assessment of a vaginal film containing TFV, daily use of two doses of film and a vaginal gel yielded comparable safety and tolerability results. The rate of AEs, including genitourinary specific complaints, was similar between TFV and placebo arms and similar to rates of AEs published for other vaginal microbicide trials of TFV.

Importantly genital, plasma, and tissue concentrations were comparable between the 40 mg TFV film and the TFV gel (loaded with 40 mg of TFV), suggesting equally-efficient drug delivery systems. The lower plasma TFV and tissue concentrations of TFV-DP achieved with the 10 mg TFV film suggest that film does not delivery drug more efficiently as one might presume due to less dilution.

The pharmacokinetic results from this study mirror results from two important trials of TFV vaginal gel. In the MTN-001 trial (MTN-001: randomized pharmacokinetic cross-over study comparing tenofovir vaginal gel and oral tablets in vaginal tissue and other compartments. *PLoS One*. 2013; 8(1):e55013), Hendrix et al. delineated the pharmacokinetics of oral and vaginal gel forms of TFV. That trial demonstrated a nearly 100-fold greater vaginal tissue concentration with vaginal dosing compared to oral dosing which suggests that the direct drug delivery to the vagina was more efficient than the oral route. In the current study, genital TFV-DP concentrations achieved with vaginal 40 mg film and 1% gel were similar to those achieved in MTN-001. In addition, the quantity of drug detected in the CVL in this study was similar to the level in cervicovaginal fluid (>1000 ng/mL) that was found to provide significant protection from HIV in CAPRISA 004 (Kashuba et al. Genital Tenofovir Concentrations Correlate With Protection Against HIV Infection in the CAPRISA 004 Trial: Importance of Adherence for Microbicide Effectiveness. *Journal of acquired immune deficiency syndromes*. Jul. 1, 2015; 69(3):264-269) and which was detected in the first study investigating the pharmacokinetics of TFV (Schwartz et al. A multi-compartment, single and multiple dose pharmacokinetic study of the vaginal candidate microbicide 1% tenofovir gel. *PLoS One*. 2011; 6(10):e25974).

In a previous study of vaginal films containing the non-nucleoside reverse transcriptase inhibitor dapivirine, 5 of 31 (16%) women did not place their films correctly into the vagina (Bunge et al. A Phase 1 Trial to Assess the Safety, Acceptability, Pharmacokinetics, and Pharmacodynamics of a Novel Dapivirine Vaginal Film. *Journal of acquired immune deficiency syndromes*. Apr. 15, 2016; 71(5):498-505). In the current study only 2 of 45 (4%) women did not correctly place their films into the vagina. The film used in the current study differed from the dapivirine film in that it was larger (2×2 inches vs 1×2 inches) and made with a different polymer type (cellulose vs polyvinyl alcohol). Understanding whether this improvement in film placement was due to film size or polymer type is an important objective and not discernable from the current data. These film characteristics differences are currently being evaluated for ease of use and correct placement.

Prior microbicide clinical trial experience has demonstrated that vaginal products can deliver drug to the tissues at risk while minimizing systemic side effects; however, it has also shown that adherence to daily use of vaginal and oral products is low in study populations at high risk of HIV infection. Adherence was slightly improved with peri-coital administration in CAPRISA-004, but not in a subsequent trial, FACTS-001. In an attempt to minimize user error and improve adherence, the focus of vaginal microbicide research has shifted to sustained delivery formulations such as vaginal rings. However, as contraceptive research has demonstrated, providing formulation and dosing options for women is critical to increase uptake. The film dosage form could provide a lower cost on-demand microbicide product for women that may be more acceptable than gels and which, as a consequence, may improve adherence.

Acceptability evaluations of vaginal gels have consistently demonstrated that one major drawback to gel use is perceived messiness and leakage. The present study substantiated previous research that found vaginal film products to have less leakage than gel products in young sexually active women. In a side-by-side acceptability study of different formulations of nonoxynol-9, women found film to be more acceptable and cited "messiness" as the main drawback to gel formulations. Coggins et al. asked women in Thailand, Zambia, the Ivory Coast, and the United States to compare the use of difference topical vaginal dosage forms, including film, suppository, gel, and foam (Women's preferences regarding the formulation of over-the-counter vaginal spermicides. *AIDS*. Jul. 30, 1998; 12(11):1389-1391). Participants used each product for four weeks and then were asked to assess the relative acceptability of each product. Most participants preferred the film and gel to suppository. In a different study of more than 1500 US women randomized to a nonoxynol-9 film, gel or suppository for contraception over a 7 month period, 42-51% of women randomized to gel reported messiness with product use as compared to 23% of film users (Raymond et al. Acceptability of five nonoxynol-9 spermicides. *Contraception*. June 2005; 71(6):438-442). This is very similar to the reported rate of product leakage in the present study.

Beyond the issue of leakage and messiness impacting acceptability, the lack of discreetness with vaginal gels may also contribute to low adherence in ways that have not been thoroughly investigated. Several secondary analyses of the vaginal gel trials have shown that partner disclosure of gel use was associated with significantly higher adherence rates. Because films are thin and dry, they have a relatively small volume and weight when compared to aqueous-based gels. This has two distinct advantages with respect to covert use: the packaging for films is much smaller and, in use, the product is associated with less leakage than gels.

The present study confirmed that films deliver as much drug to the tissues as an aqueous based gel with less leakage and a favorable acceptability profile. Importantly, for this reason, films have the potential to be a product which makes adherence easier for women. The next step in the advancement of vaginal film technology, developing films with different release patterns that may confer protection for days, rather than hours, should make film use and adherence to protocol much easier thereby providing much better protection from HIV infection.

Example 3

In view of the optimal results in terms of testing and characterization of the following formulations (Table 9):

| Ingredient | Concentration (%) for 40 mg per 2" × 2" film | Concentration (%) for 10 mg per 2" × 2" film |
| --- | --- | --- |
| Tenofovir | 2 | 0.5 |
| Hydroxyethyl cellulose (250 L Pharm) | 6 | 6 |
| Hydroxypropyl methylcellulose | 6 | 6 |
| Carboxymethylcellulose Sodium (Low Viscosity, USP) | 2 | 2 |
| Glycerin, USP | 2 | 2 |
| Sodium Hydroxide | 0.28 | 0.07 |
| MilliQ to QS | 100 | 100 | the formulations were scaled up for production. Results of testing performed on the formulations following storage for up to 24 months is presented in FIGS. 11-12. As can be seen, the films conform to ICH guidance at each time point, suggesting excellent long-term stability and the possibility of extended shelf life.

Example 4

Topical pre-exposure prophylaxis is the vaginal or rectal application of a microbicide product prior to sexual intercourse to protect against HIV infection. Microbicides can be formulated into different dosage forms such as; tablets, gels, films, and rings. The efficacy of the microbicide product in vivo is highly dependent on the efficient release of active agent from the dosage form. One dosage form which has been found to be acceptable to women is the vaginal thin film, but there is little information regarding film distribution and drug release kinetics within the vagina. The objective of this study was to evaluate the impact of film thickness on tenofovir (TFV) drug release using in vitro mechanical testing, dissolution testing and visual monitoring of product retention in a macaque model. Magnetic resonance imaging (MRI) was conducted to study product distribution in this model.

Methods: Solvent cast vaginal films containing TFV and/or gadobenate dimeglumine (GD, a contrast agent))

were intravaginally delivered to pigtail macaques. Films were produced using solvent casting with the following polymers: hydroxyethyl cellulose, hydroxypropyl methyl cellulose, and carboxymethyl cellulose. Glycerin was included as a plasticizer, and the solution also included sodium hydroxide as a base. Films were assessed for mass, thickness, water content, and puncture strength, with characteristics as follows (Table 10):

| Film Characteristics | |
|---|---|
| Mass (mg) | 88.92 ± 3.64 (max 331.94 ± 20.06) |
| Thickness (mm) | 0.09 ± 0.005 (max 0.499 ± 0.002) |
| Water Content (%) | 5.94 ± 0.28 (max 10.02 ± 1.17) |
| Puncture Strength (g/mm) | 8.58 ± 0.83 (max (3.37 ± 0.18) |
| Drug Content (TFV, mg) | 18.17 ± 1.18 (max 18.70 ± 0.69) |

Films with varied thickness were manufactured with a blue dye for visual retention studies using colposcopy. Drug release was analyzed through vaginal dacron swab collection and mass spectrometry analysis. A separate study used MRI to track film dispersal (with GD). Drug content was assessed with a Waters ACQUITY® UPLC System with a Waters Acquity UPLC BEH C18 1.7 μm 2.1×50 mm column at a wavelength of 260 nm. Mobile phase was pH 5.7 phosphate buffer in methanol at a ratio of 90:10 at a flow rate of 0.3 ml/min. Average retention time was 2.6±0.4 min. Water Content was assessed with a Karl Fischer Titration with a 890 Karl Fischer Titrando. Puncture Strength and Disintegration were assessed with a Texture Analyzer®. In vitro drug release was assessed with a USP 4 flow through SOTAX system and UPLC analysis.

As described above, assessment of retention was performed in two different ways: MRI and visual inspection. For the MRI study, one GD-labelled film was intravaginally delivered to each of four pigtail macaques. MRI was used to track the film dispersal from the point of instillation, throughout the vagina, the upper reproductive tract (URT) and rectum. Sagittal and axial sections of each macaque's pelvic cavity were obtained at 4 and 24 hours post film insertion. MRI scans were scored on a binary scale for presence versus absence of signal in the vaginal canal, ectocervix, endometrium, fallopian tubes, rectum, urethra, and periurethral tissues.

For visual retention, dyed films were identified using colposcopic imaging on days 2, 3, 4, 5, and 8. In addition, vaginal swabs were obtained at the same time points (Table 11):

| | Day 1: Base/T0 | Day 2: 24 hr post film | Day 3: 48 hr post film | Day 4: 3 d post film | Day 5: 4 d post film | Day 8: 1 wk post film |
|---|---|---|---|---|---|---|
| Place TFV film (after baseline measurements) (~100 μM or 500 μM) | ● | | | | | |
| Colposcopic image: Visualize disintegration | ● | ● | ● | ● | ● | ● |
| Vaginal swab: Document drug presence | ● | ● | ● | ● | ● | ● |

Figure 13:
FIG. 13 shows paired 4-hour and 24-hour MRI images, with vaginal canal circled, showing film placement for a film described herein.
Figure 14:
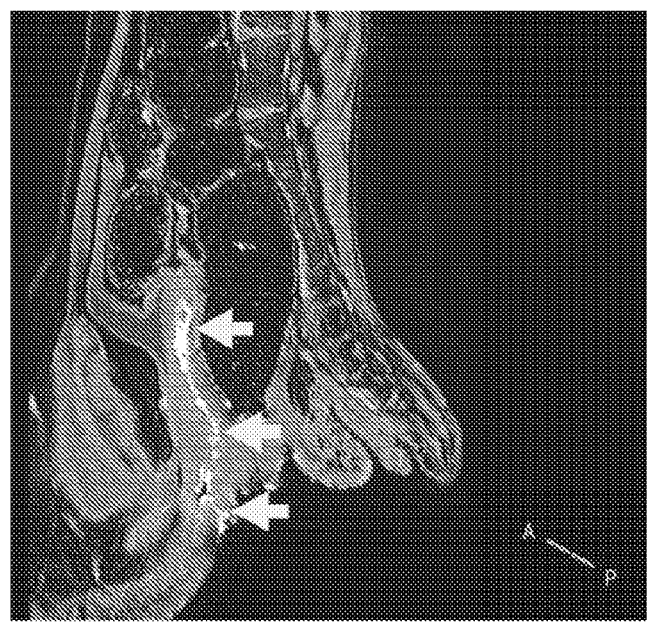
FIG. 14 shows a 4-hour MRI image with arrows identifying GD (included in the film as a contrast agent) for a film described herein.

Results: As shown above, films contained an average of 18.17 mg of TFV. Visual film retention observations in the macaque showed that increased film thickness resulted in a longer vagina film residence time. MRI studies in this same model demonstrated that GD contrast was clearly seen throughout the vagina and ectocervix at the initial time point (which was 4 hours post film placement). FIGS. 13 and 14 show localization of the TFV films using MRI. FIG. 13 shows paired 4-hour and 24-hour MRI images, with vaginal canal circled in each image. In each of four animals, MRI contrast was clearly seen throughout the vagina and ectocervix at 4 hours after placement of the vaginal film. At 24 hours, the signal was markedly reduced and present only in the vaginal canal. No evidence of contrast was noted in other areas of the genitorectal tract at either time-point. FIG. 14 shows a 4-hour image, from another animal, with GD signal highlighted by arrows. MRI contrast was clearly seen throughout the vagina, from cervix to introitus at 4 hours after placement of the vaginal film.

Figure 15:
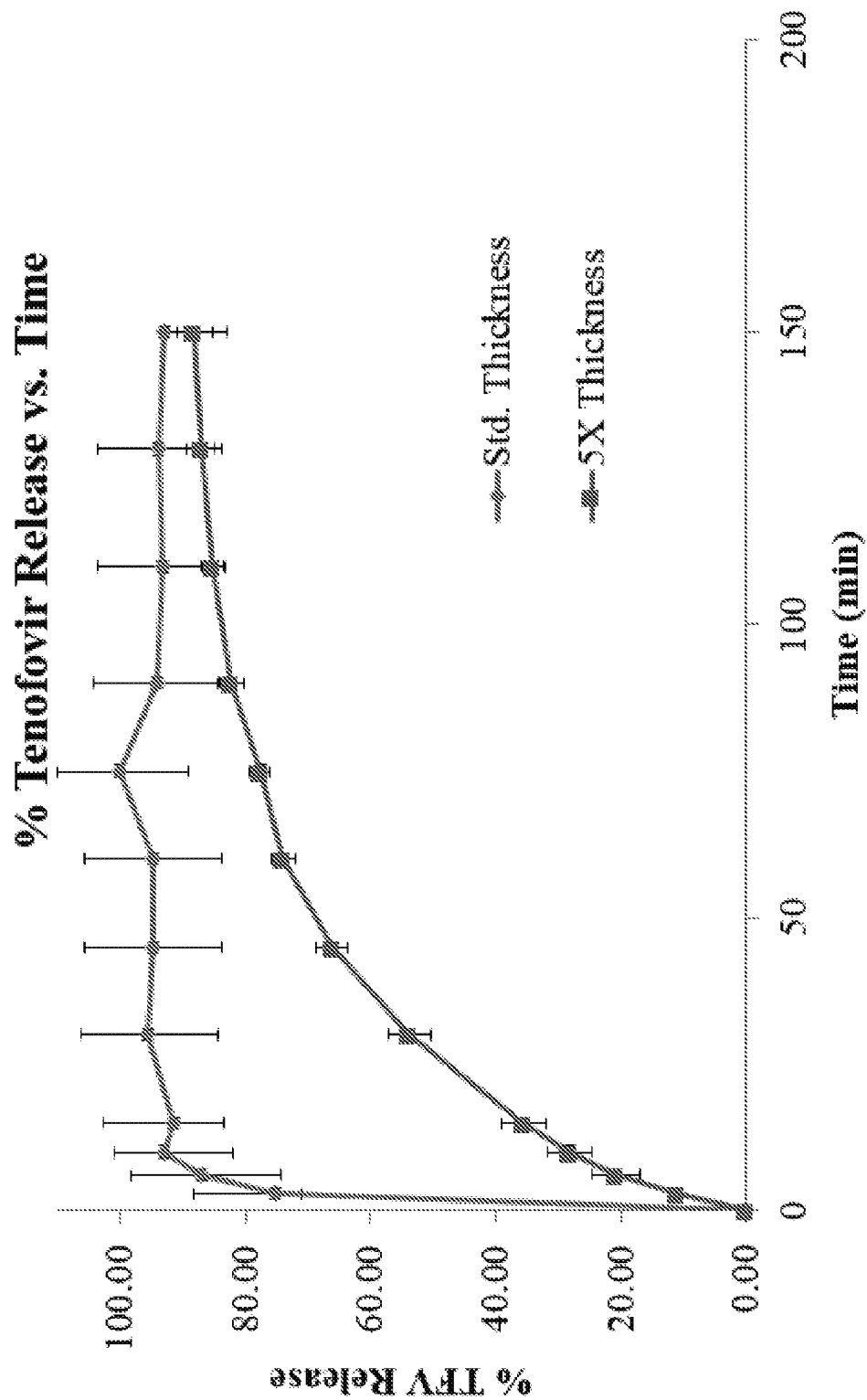
FIG. 15 shows the in vitro release profile of TFV films according to aspects of the film described herein.

FIG. 15 shows in vitro release of TFV, and that increasing film thickness prolongs the maximum time to release, suggesting that a thicker film (squares in FIG. 15) can be used to provide extended release of a therapeutic.

FIGS. 16 and 17 show visual retention and drug concentration in vaginal fluid (based on swabs) for four subjects at film placement, and days 2, 3, 4, 5, and 8. These results show that TFV is released in vivo in both thin and thick films.

Conclusions: In vivo, the vaginal film has been shown to effectively coat the vaginal and ectocervical tissues without migrating to URT or peritoneal spaces. Changes in film thickness can affect drug release profile and vagina film residence time. Data obtained suggest that the film platform may provide sustained drug release offering a wider window of protection against HIV.

The following clauses are illustrative of various aspects of the invention:

Clause 1: A dissolvable film comprising one or more cellulose polymers, a plasticizer, and a therapeutic composition.

Clause 2: The dissolvable film according to clause 1, wherein the therapeutic composition is an antiretroviral composition.

Clause 3: The dissolvable film according to clause 2, wherein the antiretroviral composition is a nucleoside reverse transcriptase inhibitor or a nonnucleoside reverse transcriptase inhibitor.

Clause 4: The dissolvable film of clause 2, wherein the antiretroviral composition comprises tenofovir or a pharmaceutically-acceptable salt thereof.

Clause 5: The dissolvable film of clause 4, wherein the antiretroviral composition further comprises dapivirine or a pharmaceutically-acceptable salt thereof.

Clause 6: The dissolvable film of any of clauses 2-5, wherein the film comprises 14% wt. of one or more cellulose polymers, 2% wt. of a plasticizer, and between 0.5 and 2% wt. of an antiretroviral composition.

Clause 7: The dissolvable film of clause 6, wherein the one or more cellulose polymers are three cellulose polymers.

Clause 8: The dissolvable film of clause 7, wherein the three cellulose polymers comprise hydroxyethyl cellulose, hydroxypropyl methyl cellulose, and carboxymethyl cellulose.

Clause 9: The dissolvable film of clause 7, wherein the three cellulose polymers comprise 1.5 to 7% wt. hydroxyethyl cellulose, 1.5 to 8% wt. hydroxypropyl methyl cellulose, and 0.5 to 6% wt. carboxymethyl cellulose.

Clause 10: The dissolvable film of clause 8 or clause 9, wherein the carboxymethyl cellulose is sodium carboxymethyl cellulose.

Clause 11: The dissolvable film of any of clauses 1-10, wherein the film releases at least 50% of the antiretroviral composition within 10 minutes of being placed intravaginally or intrarectally in a patient.

Clause 12: The dissolvable film of any of clauses 1011, wherein the film releases 100% of the antiretroviral composition within one hour of being placed intravaginally or intrarectally in a patient.

Clause 13: A dissolvable film comprising one or more cellulose polymers, a plasticizer, and an antiretroviral composition, such as a dried film prepared from an aqueous solution (QS H2O) comprising 14% wt. of one or more cellulose polymers, 2% wt. of a plasticizer, between 0.07 and 0.28% wt. of a strong base, and between 0.5 and 2% wt. of an antiretroviral composition.

Clause 14: The dissolvable film of clause 13, wherein the one or more cellulose polymers are three cellulose polymers.

Clause 15: The dissolvable film of clause 14, wherein the three cellulose polymers comprise 1.5 to 7% wt. hydroxyethyl cellulose, 1.5 to 8% wt. hydroxypropyl methyl cellulose, and 0.5 to 6% wt. carboxymethyl cellulose.

Claude 16: The dissolvable film of clause 15, wherein the three cellulose polymers comprising 6% wt. hydroxyethyl cellulose, 6% wt. hydroxypropyl methyl cellulose, and 2% wt. carboxymethyl cellulose.

Clause 17: The dissolvable film of clause 16, wherein the carboxymethyl cellulose is sodium carboxymethyl cellulose.

Clause 18: The dissolvable film of any of clauses 13-17, wherein the plasticizer comprises 2% wt. glycerin.

Clause 19: The dissolvable film of any of clauses 13-18 wherein the antiretroviral composition is tenofovir.

Clause 20: The dissolvable film of clause 19, wherein the tenofovir is tenofovir disoproxil.

Clause 21: The dissolvable film of clause 19 or clause 20, wherein the film comprises 2% wt. of tenofovir.

Clause 22: The dissolvable film of any of clauses 13-21 wherein the film further comprises dapivirine.

Clause 23: The dissolvable film of any of clauses 13-22, wherein the aqueous solution used to prepare the film comprises 0.28% wt. sodium hydroxide.

Clause 24: The dissolvable film of any of clauses 13-23, wherein the film releases at least 50% of the antiretroviral composition within 10 minutes of being placed intravaginally or intrarectally in a patient.

Clause 25: The dissolvable film of any of clauses 13-24, wherein the film releases 100% of the antiretroviral composition within one hour of being placed intravaginally or intrarectally in a patient.

Clause 26: A method of producing a dissolvable film, comprising an antiviral active agent: adding a strong base and a therapeutic composition to water under constant mixing to form a mixture; adding hydroxyethyl cellulose to the mixture and mixing until the hydroxyethyl cellulose is completely hydrated; forming a first premix of hydroxypropyl methyl cellulose and a plasticizer and adding the first premix to the mixture under mixing until the hydroxypropyl methyl cellulose is fully wetted; forming a second premix of carboxymethyl cellulose and a plasticizer and adding the second premix to the mixture under mixing until the carboxymethyl cellulose is fully wetted to form a pre-film solution, wherein the pre-film solution comprises 1.5 to 7% wt. hydroxyethyl cellulose, 1.5 to 8% wt. hydroxypropyl methyl cellulose, 0.5 to 6% wt. carboxymethyl cellulose, 0.5 to 2.4% wt. of the plasticizer, between 0.07 and 0.28% wt. of the strong base, and between 0.5 and 2% wt. of the antiretroviral composition; testing the pH of the mixture and, if necessary, adjusting the pH to between 5 and 8; applying the pre-film solution to a surface; and drying the pre-film solution to produce a film.

Clause 27: The method of clause 26, wherein the pre-film solution comprises 6% wt. hydroxyethyl cellulose, 6% wt. hydroxypropyl methyl cellulose, 2% wt. carboxymethyl cellulose, and 2% wt. of the plasticizer.

Clause 28: The method of clause 26 or clause 27, wherein the plasticizer is glycerin.

Clause 29: The method of any of clauses 26-28, wherein the therapeutic composition is an antiviral composition, optionally tenofovir.

Clause 30: The method of clause 29, wherein the tenofovir is tenofovir disoproxil.

Clause 31: The method of any of clauses 26-30, wherein the pre-film solution comprises 2% wt. tenofovir.

Clause 32: The method of any of clauses 29-31, wherein the film comprises 40 mg of tenofovir.

Clause 33: The method of any of clauses 26-32, further comprising cutting the film to 2 inch by 2 inch squares.

Clause 34: A method of producing a dissolvable tenofovir-containing film, comprising: adding 0.28% wt. sodium hydroxide and 2% wt. tenofovir disoproxil to water under constant mixing to form a mixture; adding 6% wt. hydroxyethyl cellulose to the mixture and mixing until the hydroxyethyl cellulose is completely hydrated; forming a first premix of 6% wt. hydroxypropyl methyl cellulose and glycerin and adding the first premix to the mixture under mixing until the hydroxypropyl methyl cellulose is fully wetted; forming a second premix of 2% wt. carboxymethyl cellulose and glycerin and adding the second premix to the mixture under mixing until the carboxymethyl cellulose is fully wetted to form a pre-film solution, wherein the pre-film solution comprises 2% wt. glycerin; testing the pH of the mixture and, if necessary, adjusting the pH to between 6 and 6.5; applying the pre-film solution to a heated surface; and drying the pre-film solution on the heated surface to produce a film.

Clause 35: A method of providing prophylactic protection from human immunodeficiency virus, comprising placing a dissolvable film comprising 14% wt. of one or more cellulose polymers, 2% wt. of a plasticizer, and between 0.5 and 2% wt. of an antiretroviral composition intravaginally or intrarectally in a patient.

Clause 36: The method of clause 35, wherein the film is placed intravaginally or intrarectally at least 10 minutes prior to coital activity.

Clause 37: A method of providing prophylactic protection from a herpesvirus, such as a herpes simplex virus, comprising placing a dissolvable film comprising 14% wt. of one or more cellulose polymers, 2% wt. of a plasticizer, and between 0.5 and 2% wt. of an antiretroviral composition intravaginally or intrarectally in a patient.

Clause 38: The method of clause 37, wherein the film is placed intravaginally or intrarectally at least 10 minutes prior to coital activity.

Clause 39: The method of clause 37 or clause 38, wherein the antiretroviral composition comprises tenofovir, e.g. tenofovir disoproxil.

Clause 40: The method of clause 37, wherein the herpesvirus is HSV-1.

Clause 41: The method of clause 37, wherein the herpesvirus is HSV-2.

Although the invention has been described in detail for the purpose of illustration based on what is currently considered to be the most practical aspects, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A dissolvable film comprising 6% wt. hydroxyethyl cellulose, 6% wt. hydroxypropyl methyl cellulose, and 2% carboxymethyl cellulose, a plasticizer, and 2% wt. of a nucleoside reverse transcriptase inhibitor.

2. The dissolvable film of claim 1, wherein the nucleoside reverse transcriptase inhibitor comprises tenofovir or a pharmaceutically-acceptable salt thereof.

3. The dissolvable film of claim 2, further comprising dipivefrine or a pharmaceutically-acceptable salt thereof.

4. The dissolvable film of claim 1, wherein the carboxymethyl cellulose is sodium carboxymethyl cellulose.

5. The dissolvable film of claim 1, wherein the plasticizer comprises 2% wt. glycerin.

6. This dissolvable film of claim 1, wherein the nucleoside reverse transcriptase inhibitor is tenofovir.

7. The dissolvable film of claim 6, wherein the tenofovir is tenofovir disoproxil.

8. The dissolvable film of claim 6, wherein the film further comprises dapivirine.

9. The dissolvable film of claim 1, wherein the film further comprises 0.28% wt. sodium hydroxide.

10. A dissolvable film formed from an aqueous solution comprising 6% wt. hydroxyethyl cellulose, 6% wt. hydroxypropyl methyl cellulose, 2% wt. carboxymethyl cellulose, 2% wt. glycerin, and 2% wt. tenofovir.

11. The dissolvable film of claim 5, wherein the film comprises 6% wt. hydroxyethyl cellulose, 6% wt. hydroxypropyl methyl cellulose, 2% wt. carboxymethyl cellulose, 2% wt. glycerin, and 2% wt. tenofovir, and further comprises 0.28% wt. sodium hydroxide.

* * * * *

UNITED STATES PATENT AND TRADEMARK OFFICE
CERTIFICATE OF CORRECTION

PATENT NO. : 11,793,765 B2
APPLICATION NO. : 16/494804
DATED : October 24, 2023
INVENTOR(S) : Lisa Cencia Rohan Page 1 of 1

It is certified that error appears in the above-identified patent and that said Letters Patent is hereby corrected as shown below:

In the Specification

Column 1, Line 8, delete "Mar. 29, 2019" and insert therefor -- Mar. 27, 2018 --;

In the Claims

Column 29, Line 29, Claim 1, delete "cellulose, 6% wt. hydroxypropyl methyl cellulose, and 2%" and insert therefor -- cellulose, 6% wt. hydroxypropyl methyl cellulose, 2% --; and Column 20, Line 12, Claim 6, delete "This" and insert therefor -- The --.

Signed and Sealed this
Seventh Day of January, 2025

Derrick Brent
*Acting Director of the United States Patent and Trademark Office*